United States Patent
Nolte et al.

(10) Patent No.: US 10,426,348 B2
(45) Date of Patent: Oct. 1, 2019

(54) USING DIFFERENTIAL TIME-FREQUENCY TISSUE-RESPONSE SPECTROSCOPY TO EVALUATE LIVING BODY RESPONSE TO A DRUG

(71) Applicant: Purdue Research Foundation, West Lafayette, IN (US)

(72) Inventors: David D. Nolte, Lafayette, IN (US); John J. Turek, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 449 days.

(21) Appl. No.: 13/760,827

(22) Filed: Feb. 6, 2013

(65) Prior Publication Data

US 2013/0144151 A1 Jun. 6, 2013
US 2017/0156598 A9 Jun. 8, 2017

Related U.S. Application Data

(63) Continuation-in-part of application No. 12/874,855, filed on Sep. 2, 2010, now Pat. No. 8,886,295, which is a continuation of application No. PCT/US2009/036124, filed on Mar. 5, 2009, application No. 13/760,827, filed on Feb. 6, 2013, which is a continuation-in-part of application No. 13/704,464, filed as application No. PCT/US2011/040954 on Jun. 17, 2011, now Pat. No. 9,977,859, application No. 13/760,827, filed on Feb. 6, 2013, which is a continuation-in-part of application No. 13/704,438, filed as application No. PCT/US2011/040959 on Jun. 17, 2011, now Pat. No. 9,514,271.

(60) Provisional application No. 61/034,028, filed on Mar. 5, 2008, provisional application No. 61/397,885, filed on Jun. 17, 2010.

(51) Int. Cl.
*A61B 5/00* (2006.01)
*G03H 1/08* (2006.01)
*G03H 1/04* (2006.01)

(52) U.S. Cl.
CPC ......... *A61B 5/0075* (2013.01); *G03H 1/0443* (2013.01); *G03H 1/08* (2013.01); *G03H 2210/62* (2013.01)

(58) Field of Classification Search
CPC ...... A61B 5/0075; A61B 5/00; G03H 1/0443; G03H 1/08; G03H 2210/62
See application file for complete search history.

(56) References Cited

U.S. PATENT DOCUMENTS

| | | |
|---|---|---|
| 4,674,824 A | 6/1987 | Goodman et al. |
| 5,682,262 A | 10/1997 | Wefers et al. |
| 6,014,204 A | 1/2000 | Prahl et al. |
| 6,016,223 A | 1/2000 | Suzuki et al. |
| 6,053,613 A | 4/2000 | Wei et al. |
| 6,144,449 A | 11/2000 | Knuettel et al. |
| 6,195,168 B1 | 2/2001 | De Lega et al. |
| 6,262,818 B1 | 7/2001 | Cuche et al. |
| 6,268,921 B1 | 7/2001 | Seitz et al. |
| 6,556,305 B1 | 4/2003 | Aziz et al. |
| 7,057,720 B2 | 6/2006 | Caracci et al. |
| 7,148,970 B2 | 12/2006 | de Boer |
| 7,327,463 B2 | 2/2008 | Alphonse |
| 7,364,296 B2 | 4/2008 | Miller et al. |
| 7,452,681 B2 | 11/2008 | Amaral et al. |
| 7,474,407 B2 | 1/2009 | Gutin |
| 7,551,293 B2 | 6/2009 | Yelin et al. |
| 8,379,218 B2 | 2/2013 | Deck et al. |
| 8,508,746 B2 | 8/2013 | Wax et al. |
| 2004/0089800 A1 | 5/2004 | Jackman |
| 2004/0101168 A1 | 5/2004 | Kostrzewski et al. |
| 2005/0121596 A1 | 6/2005 | Kam et al. |
| 2005/0239111 A1* | 10/2005 | Van Rhee et al. ............ 435/6 |
| 2006/0243831 A1 | 11/2006 | Gonzalez-Zugasti et al. |

(Continued)

FOREIGN PATENT DOCUMENTS

| | | |
|---|---|---|
| JP | 2009053578 A | 3/2009 |
| WO | WO2009111609 A2 | 9/2009 |
| WO | WO 2012005952 A2 | 1/2012 |

OTHER PUBLICATIONS

Chen, "Optical Doppler Tomography," IEEE J Selected Topics in Quantum Electronics, vol. 5, p. 1134-1142, 1999.*
Cunningham, "Kernel decomposition of time-frequency distributions," Signal Processing, IEEE Transactions, vol. 42.6, p. 1425-1442, 1994.*
Yu, "Time-dependent speckle in holographic optical coherence imaging and the health of tumor tissue," Optics Letters, vol. 29, p. 68-70, 2004.*
Murialdo, "Application of a laser speckle method for determining chemotactic responses of Pseudomonas aeruginosa towards attractants," International Society for Optics and Photonics, 6 pages, 2006.*
Marks, "Autofocus algorithm for dispersion correction in optical coherence tomography," Applied Optics, vol. 42, p. 3038-3046, 2003.*

(Continued)

*Primary Examiner* — G Steven Vanni
(74) *Attorney, Agent, or Firm* — Bose McKinney & Evans LLP

(57) ABSTRACT

A phenotypic profiling method for drug/dose physiological response of living bodies utilizes feature recognition to segment the information in time-frequency tissue-response spectrograms to construct N-dimensional feature vectors. The feature vectors are used to generate a correlation matrix among a large number of different stimuli in the form of drugs, doses and conditions. Multi-dimensional scaling is applied to the correlation matrix to form a two-dimensional map of response relationships that retains rank distances from the higher-dimensionality feature matrix. The two-dimensional phenotypic profile space displays compact regions indicative of particular physiological responses, such as regions of enhanced active transport, membrane undulations and blebbing.

27 Claims, 20 Drawing Sheets
(20 of 20 Drawing Sheet(s) Filed in Color)

(56) References Cited

U.S. PATENT DOCUMENTS

| | | |
|---|---|---|
| 2007/0073156 A1 | 3/2007 | Zilberman et al. |
| 2007/0236687 A1 | 10/2007 | Mikuriya et al. |
| 2008/0018966 A1 | 1/2008 | Dubois et al. |
| 2008/0097183 A1 | 4/2008 | Monro |
| 2008/0277595 A1 | 11/2008 | Lundquist et al. |
| 2009/0018436 A1 | 1/2009 | Gey Van Pittius et al. |
| 2009/0073529 A1 | 3/2009 | Imai |
| 2009/0221920 A1 | 9/2009 | Boppart et al. |
| 2010/0027857 A1 | 2/2010 | Wang |
| 2010/0065751 A1 | 3/2010 | Harra et al. |
| 2010/0141829 A1 | 6/2010 | Jalali et al. |
| 2010/0141954 A1 | 6/2010 | Kobayashi |
| 2011/0096291 A1 | 4/2011 | Buckland et al. |

OTHER PUBLICATIONS

Jackson, "Similarity coefficients: measures of co-occurrence and association or simply measures of occurrence?" American Naturalist, vol. 133, p. 436-453, 1989.*

Qeli, "Visualizing time-varying matrices using multidimensional scaling and reorderable matrices," IEEE Proceedings of the Eighth International Conference on Information Visualisation (IV '04), p. 561-567, 2004.*

Klock, "Data visualization by multidimensional scaling: a deterministic annealing approach," Pattern Recognition, vol. 33, p. 651-669, 2000.*

Jeong, "Functional imaging by dynamic speckle in digital holographic optical coherence imaging," Proc. of SPIE, vol. 64291, p. 64291V-1 through 64291V-9, Feb. 2007.*

Gillies, R. J. and Gatenby, R.A. "Hypoxia and adaptive landscapes in the evolution of carcinogenesis," Cancer and Metastasis Reviews 26(2): 311-317, 2007.

Sullivan, R. and Graham, C.H., "Hypoxia-driven selection of the metastatic phenotype," Cancer and Metastasis Reviews 26(2): 319-331, 2007.

Gort, E.H., et al., "Hypoxic regulations of metastasis via hypoxia-inducible factors," Current Molecular Medicine 8(1): 60-67, 2008.

Klymkowsky, M.W. and Savagner, P., "Epithelial-Mesenchymal Transition A Cancer Researcher's Conceptual Friend and Foe," American Journal of Pathology 174(5): 1588-1593, 2009.

Yan, W., et al., "PI3 kinase/Akt signaling mediates epithelial-mesenchymal transition in hypoxic hepatocellular carcinoma cells," Biochemical and Biophysical Research Communications 382(3): 631-636, 2009.

Farhat, G., et al., "Detecting apoptosis using dynamic light scattering with optical coherence tomography," Journal of Biomedical Optics 16(7), 2011.

Johnson, R.A. "Applied Multivariate Statistical Analysis," Prentice Hall, 2001.

PCT/US2009/036124, Mar. 2009, Written Opinion.

Fujimoto, J.G., "Optical coherence tomography for ultrahigh resolution in vivo imaging," Nature Biotechnology, 2003, 21 (11): p. 1361-1367.

Fercher, A.F., et al., "Optical coherence tomography-principles and applications," Reports on Progress in Physics, 2003, 66(2): p. 239-303.

Hyde, S.C.W., et al., "Depth-resolved holography through turbid media using photorefraction, " IEEE J. Sel. Top. Quant. Electron., 1996 2: p. 965.

Jones, R., et al., "Holographic storage and high background imaging using photorefractive multiple quantum wells," Appl. Phys. Lett., 1996, 69: p. 1837.

Jones, R., et al., "Real-time 3-D holographic imaging using photorefractive media including multiple-quantum-well devices," IEEE J. Sel. Top. Quant. Electron., 1998 4(2):p. 360-9.

Tziraki, M., et al., "Photorefractive Holography for Imaging through turbid media using low coherence light," Appl. Phys. B. 2000 70: p. 151.

Nolte, D.D., "Semi-insulating semiconductor heterostructures: Optoelectronic properties and applications," J. Appl. Phys., 1999 85: p. 6259.

Nolte, D.D., et al., "Adaptive Beam Combining and Interferometry using Photorefractive Quantum Wells," J. Opt. Soc. Am. B, 2001, 18: p. 195-205.

Jeong, K., et al., "Fourier-domain holographic optical coherence imaging of tumor spheroids and mouse eye," Appl. Opt. 2005 44(10): p. 1798-1806.

Yu, P., et al., "Holographic optical coherence imaging of rat osteogenic sarcoma tumor spheroids," Applied Optics 2004 43(25): p. 4862-4873.

Poon, T.C., T. Yatagai, and W. Juptner, "Digital holography-coherent optics of the 21st century," Introduction Applied Optics, 2006, 45(5): p. 821-821.

Schnars, U. and W.P.O. Juptner, " Digital recording and numerical reconstruction of holograms," Measurement Science & Technology, 2002 13(9): p. R85-R101.

De Ridder, L., "Autologous confrontation of brain tumor derived spheroids with human dermal spheroids," Anticancer Res., 1997, 17: p. 4119-4120.

Groebe, K. and Mueller-Klieser, "On the relation between size of necrosis and diameter of tumor spheroids," Int. J. Radiat. Oncol. Bio. Phys., 1996, 34: p. 395-401.

Hamamoto, R., et al., "Differentiation and proliferation of primary rat hepatocytes cultured as spheroids," J. Biochem (Tokyo), 1998 124: p. 972-979.

Hamilton, G., "Multicellular spheroids as an in vitro tumor model," Cancer Lett. 1998 131: p. 29-34.

Hargrave, P., et al., "Optical properties of multicellular tumor spheroids," Phys. Med. Biol., 1996, 41: p. 1067-1072.

Kunz-Schughart, L.A., M. Kreutz, and R. Knuechel, "Multicellular spheroids a three-dimensional in vitro culture system to study tumor biology," Int. J. Exp. Pathol, 1998 79: p. 1-23.

Kunz-Schughart, L.A., "Multicellular tumor spheroids: intermediates between monolayer culture and in vitro tumor," Cell Biology International, 1999, 23(3): p. 157-161.

Mueller-Klieser, W., Biophys. J., 1984, 46: p. 343-348.

Freyer, P., et al., Cancer Research, 1991, 51: p. 3831-3837.

Mueller-Klieser, W., Am. J. Physiol., 1997 (273): p. 1109-1123.

Vale, R.D., "The molecular motor toolbox for intracellular transport," Cell, 2003 112(4): p. 467-480.

Vale, R.D. and R.A. Milligan, "The way things move: Looking under the hood of molecular motor proteins," Science, 2000, 288(5463): p. 88-95.

Karsenti, E. and I. Vernos, "Cell cycle—The mitotic spindle: A self-made machine," Science 2001 294 (5542): p. 543-547.

Hirokawa, N., "Kinesin and dynein superfamily proteins and the mechanism of organelle transport," Science, 1998 279 (5350): p. 519-526.

Desai, A. and T.J. Mitchison, "Microtubule polymerization dynamics,." Annual Review of Cell and Developmental Biology, 1997, 13: p. 83-117.

Peterson, J.R. and T.J. Mitchison, "Small molecules, big impact: A history of chemical inhibitors and the cytoskeleton," Chemistry & Biology, 2002 9(12): p. 1275-1285.

Jordan, M.A. and L. Wilson, "Microtubules and actin filaments: dynamic targets for cancer chemotherapy," Current Opinion in Cell Biology, 1998 10(1): p. 123-130.

Pollard, T.D. and G.G. Borisy, "Cellular motility driven by assembly and disassembly of actin filaments," Cell, 2003 112(4): p. 453-465.

Cukierman, E., et al., "Taking cell-matrix adhesions to the third dimension," Science, 2001 294(5547): p. 1708-1712.

Webb, D.J. and A.F. Horwitz, "New dimensions in cell migration," Nat Cell Biol, 2003 5(8): p. 690.

Moerner, W.E. and D.P. Fromm, "Methods of single-molecule fluorescence spectroscopy and microscopy," Review of Scientific Instruments, 2003 74(8): p. 3597-3619.

Webb, R.H., "Confocal optical microscopy," Reports on Progress in Physics, 1996 59(3): p. 427-471.

(56) References Cited

OTHER PUBLICATIONS

Cahalan, M.D., et al., "Two-photon tissue imaging: Seeing the immune system in a fresh light," Nature Reviews Immunology, 2002 2(11): p. 872-880.
Konig, K., "Multiphoton microscopy in life sciences," Journal of Microscopy-Oxford, 2000 200: p. 83-104.
Sharpe, J., et al., "Optical projection tomography as a tool for 3D microscopy and gene expression studies," Science 2002 296(5567): p. 541-545.
Huisken, J., et al., "Optical sectioning deep inside live embryos by selective plane illumination microscopy," Science 2004 305(5685): p. 1007-1009.
Gustafsson, M.G.L., "Nonlinear structured-illumination microscopy. Wide-field fluorescence imaging with theoretically unlimited resolution," Proceedings of the National Academy 2005.
Klar, T.A., et al., "Fluorescence microscopy with diffraction resolution barrier broken by stimulated emission," Proceedings of the National Academy of Sciences of the United States. 2000.
Cailleau, R.M., et al., "Breast tumor cell lines from pleural effusions," J. Natl. Cancer Inst., 1974 53: p. 661-674.
Kaighn, M.E., "Establishment and characterization of a human prostatic carcinoma cell line (PC-3)," Invest. Urol., 1979 17: p. 16-23.
Knowles, B.B., "Human hepatocellular carcinoma cell lines secrete the major plasma proteins and hepatitis B surface antigen," Science, 1980 209: p. 497-499.
Lee, G.Y., et al., "Three-dimensional culture models of normal and malignant breast epithelial cells," Nat. Melthods, 2007 4: p. 359-65.
Kunz-Schughart, L.A., et al., "The use of 3-D cultures for high-throughput screening: The multicellular spheroid model," Journal of Biomolecular Screening, 2004 9(4): p. 273-28.
Walenta, S., et al., "Metabolic Imaging in Multicellular Sphenoids of Oncogene-transfected Fibroblasts," J. Histochemistry and Cytochemistry 2000 48: p. 509-522.
Jackson, J.R., et al., "Targeted anti-mitotic therapies: can we improve on tubulin agents?" Nature Reviews Cancer, 2007 7(2): p. 107-117.
Schmitt, J.M., "Optical coherence tomography (OCT): A review," IEEE Journal of Selected Topics in Quantum Electronics, 1999 5(4): p. 1205-1215.
Hyde, S.C.W., et al., "Sub-100 Micron Depth-Resolved Holographic Imaging Through Scattering Media in the Near-Infrared," Optics Letters 1995 20(22): p. 2330-2332.
Jeong, K., "Holographic Optical Coherence Imaging of Living Tissue," 2007, Proquest Publishing, pp. 1-205.
Jeong, et al., "Functional Imaging by Dynamic Speckle in Digital Holographic Optical Coherence Imaging," published online Feb. 7, 2007, Proc. of SPIE, vol. 6429, citation.
Jeong, et al., "Digital Holographic Optical Coherence Imaging of Tumor Tissue," 2006, Proc. of SPIE, Voi. 6079.
Biester, "Plate:vision—The System of Many Talents," Innovation 12, 2002, pp. 1-2.
Yu, "Time-dependent speckle in holographic optical coherence imaging and the health of tumor tissue," Optics Letters, vol. 29, pp. 68-70, 2004.
Sendra, "Decomposition of biospeckle images in temporary spectral bands," Optics Letters, vol. 30, pp. 1641-1643, 2005.
Hu, "Automated interpretation of subcellular patterns from immunofluorescence microscopy," J Immunological Methods, vol. 290, pp. 93-105, 2004.
Jeong, "Volumetric motility-contrast imaging of tissue response to cytoskeletal anti-cancer drugs," Optics Express, vol. 15, pp. 14057-14064, 2007.
Abraham, "High content screening applied to large-scale cell biology," Trends in Biotechnology, vol. 22, pp. 15-22, 2004.
An, R, et al., "Identify Tissue Mitosis Using Spectral Finger Prints Under Voxel-Based Spectrogram," Biomedical Applications of Light Scattering VI, vol. 8230, A.P. Wax and V. Backman, Eds., ed, 2012 (8 pages).
An, R., et a., "Label-free Mitosis Detection in Tumor Spheroids Using Tissue Dynamics Imaging," Dynamics and Fluctuations in Biomedical Photonics VII, vol. 8222, V.V. Tuchin Ed., ed, 2012 ( 9 pages).
Jeong, et al., "Fourier Domain digital holographic optical coherence imaging of living tissue," Optical Society of America, 2007, pp. 4999-5008.
Dailey et al., "Confocal Microscopy of Living Cells," Handbook of Biological Confocal Microscopy, 3rd Ed., SpringerScience+Business Media, New York, 2006, entire document retrieved from the internet, www.3dcourse.ubc.ca/2011/docs/chapters/PHC19.pdf.
International Search Report corresponding to international application No. PCT/US2011/040954, dated Oct. 17, 2011 ( 6 pages).
Ainsworth, C., "Networking for New Drugs," Nature Medicine, vol. 17, pp. 1166-1168, Oct. 2011.
Keith, C.T., et al., "Multicomponent therapeutics for networked systems," Nature Reviews Drug Discovery, vol. 4, pp. 71-U10, Jan. 2005.
Swinney, D.C. and Anthony, J., "How were new medicines discovered?" Nature Reviews Drug Discovery, vol. 10, pp. 507-519, Jul. 2011.
Hamer, P. et al., "Organotypic Gilioma Spheroids for Screening of Experimental Therapies: How Many Spheroids and Sections are Required?" Cytometry Part A, vol. 75A, pp. 528-534, Jun. 2009.
Poland, J., et al., "Comparison of protein expression profiles between monolayer and spheroid cell culture of HT-29 cells revealed fragmentation of CK18 in three-dimensional cell culture," Electrophoresis, vol. 23, pp. 1174-1184, Apr. 2002.
Dardousis, K., et al., "Identification of differentially expressed genes involved win the formation of multicellular tumor spheroids by HT-29 colon carcinoma cells," Molecular Therapy, vol. 15, pp. 94-102, Jan. 2007.
Cody, N.A.L., et al. "Influence of monolayer, spheroid, and tumor growth conditions on chromosome 3 gene expression in tumorigenic epithelial ovarian cancer cell lines," Bmc Medical Genomics, vol. 1, Aug. 7, 2008.
Zietarska, M.,et al., "Molecular description of a 3D in vitro model for the study of epithelial ovarian cancer (EOC)," Molecular Carcinogenesis, vol. 46, pp. 872-885, Oct. 2007.
Chang, T.T. and Hughes-Fulford, M., "Monolayer and Spheroid Culture of Human Liver Hepatocellular Carcinoma Cell Line Cells Demonstrate Distinct Global Gene Expression Patterns and Functions Phenotypes," Tissue Engineering Part A, vol. 15, pp. 559-567, Mar. 2009.
Shimada, M., et al., Characteristic gene expression induced by polyurethane foam/spheroid culture of hepatoma cell line, Hep G2 as a promising cell source for bioartificial liver, Hepato-Gastroenterology, vol. 54, pp. 814-820, Apr.-May 2007.
Yamashita, Y. et al, "cDNA microarray analysis in hepatocyte differentiation in Huh 7 cells," Cell Transplantation, vol. 13, pp. 793-799, 2004.
Gaedtke, L., et al., "Proteomic analysis reveals differences in protein expression in shperoid versus monolayer cultures of low-passage colon carcinoma cells," Journal of Proteome Research, vol. 6, pp. 4111-4118, Nov. 2007.
Frankel, A., et al., "Abrogation of taxol-induced G(2)-M arrest and apoptosis in human ovarian cancer cells grown as multicellular tumor spheroids," Cancer Research, vol. 57, pp. 2388-2393, Jun. 15, 1997.
Hazlehurst, L. A., et al., "Role of the tumor microenvironment in mediating de novo resistance to drugs and physiological mediators of cell death," Oncogene, vol. 22, pp. 7396-7402, Oct. 20, 2003.
Serebriiskii, I., et al., Fibroblast-derived 3Dmatrix differentially regulates the growth and drug-responsiveness of human cancer cells, Matrix Biology, vol. 27, pp. 573-585, Jul. 2008.
David, L., et al., "Hyaluronan hydrogel: An appropriate three-dimensional model for evaluation of anticancer drug sensitivity," Acta Biomaterialia, vol. 4, pp. 256-263, Mar. 2008.
Youngquist, R.C., et al., "Optical coherence-domain reflectometry: a new optical evaluation technique," Opt. Lett. vol. 12, p. 158, 1987.
Suissa, M., et al., "Internal dynamics of a living cell nucleus investigated by dynamic light scattering," European Physical Journal E, vol. 26, pp. 435-448, Aug. 2008.

(56) References Cited

OTHER PUBLICATIONS

Nan, X.L., et al., "Organelle tracking in a living cell with microsecond time resolution and nanometer spatial precision," Chemphyschem, vol. 9, pp. 707-712, Apr. 4, 2008.
Karnaky, K.J., et al., "Video-Enhanced Microscopy of Organelle Movement in an Intact Epithelium," Journal of Morphology, vol. 213, pp. 21-31, Jul. 1992.
Brazhe, N.A., et al., "Unraveling cell processes: Interference imaging interwoven with data analysis," Journal of Biological Physics, vol. 32, pp. 191-208, Oct. 2006.
Trinczek, B., et al., "Tau regulates the attachment/detachment but not the speed of motors in microtubule-dependent transport of single vesicles and organelles," Journal of Cell Science, vol. 112, pp. 2355-2367, Jul. 1999.
Brochard, F. and Lennon, J.F., "Frequency Spectrum of Flicker Phenomenon in Erythrocytes," Journal De Physique, vol. 36, pp. 1035-1047, 1975.
Strey, H. and Peterson, M., "Measurement of Erythrocyte-Membrane Elasticity by Flicker Eigenmode Decomposition," Biophysical Journal, vol. 69, pp. 478-488, Aug. 1995.
Zilker, A., et al., "Spectral-Analysis of Erythrocyte Flickering in the 0.3-4-Mu-M-1 Regime by Microinterferometry Combined with Fast Image-Processing," Physical Review A, vol. 46, pp. 7998-8002, Dec. 15, 1992.
Peterson, M.A., et al., "Theoretical and Phase-Contrast Microscopic Eigenmode Analysis of Erythrocyte Flicker-Amplitudes," Journal De Physique Ii, vol. 2, pp. 1273-1285, May 1992.
Yoon, Y.Z., et al., "Flickering Analysis of Erythrocyte Mechanical Properties: Dependence on Oxygenation Level, Cell Shape, and Hydration Level," Biophysical Journal, vol. 97, pp. 1606-1615, Sep. 16, 2009.
Evans, J., et al., "Fluctuations of the red blood cell membrane: Relation to mechanical properties and lack of ATP dependence," Biophysical Journal, vol. 94, pp. 4134-4144, May 15, 2008.
Racine, V. et al., "Visualization and quantification of vesicle trafficking on a three-dimensional cytoskeleton network in living cells," Journal of Microscopy-Oxford, vol. 225, pp. 214-228, Mar. 2007.
Ifeocher, E. and Jervis, B., Digitial Signal Processing: A Practical Approach, Prentice Hall.
Nolte, D.D., et al., "Holographic tissue dynamics spectroscopy," Journal of Biomedical Optics 16(8): 087004-087013, 2011.
Andrepoulos, B., et al., "A roadmap of clustering algorithms: finding a match for a biomedical application," Briefings in Bioinformatics 10(3): 297-314, 2009.
Lampert, T.A. and O'Keefe, S.E.M. "A survey of spectrogram track detection algorithms," Applied Acoustics 71(2): 87-100, 2010.
Venkatasubramanian, R., et al., "Incorporating energy metabolism into a growth model of multicelluar tumor spheroids," Journal of Theoretical Biology 242(2): 440-453, 2006.
Mellor, H.R. et al., "A model of quiescent tumour microregions for evaluating multicellular resistatnce to chemotherapeutic drugs," British Journal of Cancer 93(3): 302-309, 2005.
Fayad, W., et al., "Identification of Agents that Induce Apoptosis of Multicellular Tumour Spheroids: Enrichment for Mitotic Inhibitors with Hydrophobic Properties," Chemical Biology & Drug Design 78(4): 547-557, 2011.
Zhou, J.T. et al., "Tumor hypoxia and cancer progression," Cancer Letters 237(1): 10-21, 2006.
K.A. Giuliano et al., Advances in High Content Screening for Drug Discovery, Assay and Drug Development Technologies, 2003, pp. 565-577, vol. 1.
J. K. Morelli et al., Validation of an In Vitro Screen for Pospholipidosis Using a High-Content Biology Platform, Cell Biology and Toxicology, 2006, pp. 15-27, vol. 22.
P. J. O'Brien et al., High Concordance of Drug-Induced Human Hepatotoxicity with In Vitro Cytotoxicity Measured in a Novel Cell-Based Model Using High Content Screening, Archives of Toxicology, 2006, pp. 580-604, vol. 80.
J. Packeisen et al., Tissue Microarrays: A New Approach for Quality Control in Immunohistochemistry, Journal of Clinical Pathology, 2002, pp. 613-615, vol. 55.
S. M. Moghimi et al., Nanomedicine: Current Status and Future Prospects, FASEB Journal, 2005, pp. 311-330, vol. 19.
J. N. Anker et al., Biosensing with Plasmonic Nanosensors, Nature Materials, 2008, pp. 442-453, vol. 7.
X. H. Gao et al., In Vivo Cancer Targeting and Imaging with Semiconductor Quantum Dots, Nature Biotechnology, 2004, pp. 969-976, vol. 22.
S. T. Yang et al., Microbioreactors for High-Throughput Cytotoxicity Assays, Current Opinion in Drug Discovery & Development, 2008, pp. 111-127, vol. 11.
M. Schindler et al., Living in Three Dimensions—3D Nanostructured Environments for Cell Culture and Regenerative Medicine, Cell Biochemistry and Biophysics, 2006, pp. 215-227, vol. 45.
S. Huang et al., The Structural and Mechanical Complexity of Cell-Growth Control, Nature Cell Biology, 1999, pp. E131-E138, vol. 1.
S. Lelievre et al., Extracellular Matrix Signaling from the Cellular Membrane Skeleton to the Nuclear Skeleton: A Model of Gene Regulation, Recent Progress in Hormone Research—Proceedings of the 1995 Conference, 1996, pp. 417-432, vol. 51.
F. Pampaloni et al., The Third Dimension Bridges the Gap Between Cell Culture and Live Tissue, Nature Reviews Molecular Cell Biology, 2007, pp. 839-845, vol. 8.
F. Helmchen et al., Deep Tissue Two-Photon Microscopy, Nature Methods, 2005, pp. 932-940, vol. 2.
S. Lelievre et al., Three Dimensional Cell Culture: The Importance of Microenvironment in Regulation of Function, Encyclopedia of Molecular Cell Biology and Molecular Medicine, 2005, pp. 383-420, 2 ed., vol. 14, Wiley.
M. Laubscher et al., Video-Rate Three-Dimensional Optical Coherence Tomography, Optics Express, 2002, pp. 429-435, vol. 10.
A. Dubois et al., Ultrahigh-Resolution Full-Field Optical Coherence Tomography, Applied Optics, 2004, pp. 2874-2883, vol. 43.
B. Karamata et al., Multiple Scattering in Optical Coherence Tomography. II. Experimental and Theoretical Investigation of Cross Talk in Wide-Field Optical Coherence Tomography, Journal of the Optical Society of America, 2005, pp. 1380-1388, vol. 22.
A. Abbott, Biology's New Dimension, Nature, 2003, pp. 870-872, vol. 424.
Bashkansky et al., Statistics and Reduction of Speckle in Optical Coherence Tomography, Optics Letters, 2000, pp. 545-547, vol. 25.
S. O. Uppal et al., Pattern Analysis of Microtubule-Polymerizing and -Depolymerizing Agent Combinations as Cancer Chemotherapies, Int. J. Oncol., 2007, pp. 1281-1291, vol. 31.
Fercher, A.F., et al., Optical coherence tomography—principles and applications, Reports on Progress in Physics, 2003, pp. 239-303, vol. 66.
Jeong, K., et al., Fourier-domain holography in photorefractive quantum-well films, Applied Optics, 2004, pp. 3802-3811 vol. 43.
Yu, P., et al., Time-Dependent Speckle in Holographic Optical Coherence Imaging and the Health of Tumor Tissue, Opt. Lett., 2004, pp. 68-70, vol. 29.
Kunz-Schughart, L.A., Multicellular tumor spheroids: intermediates between monolayer culture and in vivo tumor, Cell Biology International, 1999, pp. 157-161, vol. 23.
Gustafsson, M.G.L., Nonlinear structured-illumination microscopy: Wide-field fluorescence imaging with theoretically unlimited resolution, Proceedings of The National Academy of Sciences of The United States of America, 2005, pp. 13081-13086, vol. 102.
Klar, T.A., et al., Fluorescence microscopy with diffraction resolution barrier broken by stimulated emission, Proceedings of The National Academy of Sciences of The United States of America, 2000, pp. 8206-8210, vol. 97.
M. J. Bissell et al., A breast cancer progression model: the importance of three-dimensional tissue architecture and metalloproteinases, Breast Cancer Research, Jun. 2005, at S15, vol. 7.
C. Bremer et al., Optical-based molecular imaging: contrast agents and potential medical applications, European Radiology, 2003, pp. 231-243, vol. 13.

(56) References Cited

OTHER PUBLICATIONS

W. Mueller-Klieser, Three-dimensional cell cultures: from molecular mechanisms to clinical applications, Am. J. Physiol., 1997, pp. 1109-1123.
P. C. Li et al., Imaging cerebral blood flow through the intact rat skull with temporal laser speckle imaging, Optics Letters, 2006, pp. 1824-1826, vol. 31.
J. M. Schmitt et al., Speckle in Otical Coherence Tomography, J. Biomed. Opt., 1999, pp. 95-105, vol. 4.
B. Karamata et al., Speckle Statistics in Optical Coherence Tomography, J. Opt. Soc. Am., 2005, pp. 593-596, vol. 22.
M. Pircher et al., Speckle Reduction in Optical Coherence Tomography by Frequency Compounding, J. Biomed. Opt., 2003, pp. 565-569, vol. 8.
N. Iftimia et al., Speckle Reduction in Optical Coherence Tomography by "Path Length Encoded" Angular Compounding, J. Biomed. Opt., 2003, pp. 260-263, vol. 8.
D. P. Popescu et al., Speckle Noise Attenuation in Optical Coherence Tomography by Coumpounding Images Acquired at Differenct Positions of the Sample, Opt. Comm., 2007, pp. 247-251, vol. 269.
P. Yu et al., Holographic Optical Coherence Imaging of Tumor Spheroids, Appl. Phys. Lett., 2003, pp. 575-577, vol. 83.
T. R. Hillman et al., Correlation of static speckle with sample properties in optical coherence tomography, Opt. Lett., 2006, pp. 190-192, vol. 31.
Y. Park et al.,Speckle-field digital holographic microscopy, Opt. Express, Jul. 20, 2009, pp. 12285-12292, vol. 17.
A. K. Dunn et al., Dynamic Imaging of Cerebral Blood Flow Using Laser Speckle, J. Cereb. Blood Flow Metab., 2001, pp. 195-201, vol. 21.
S. Yuan et al., Determination of optimal exposure time for imaging of blood flow changes with laser speckle contrast imaging, Appl. Opt., Apr. 2005, pp. 1823-1830, vol. 44.
J. D. Briers, Laser Speckle Contrast Imaging for Measuring Blood Flow, Opt. Appl., 2007, pp. 139-152, vol. 37.
D. D. Duncan et al., Can Laser Speckle Flowmetry Be Made a Quantitative Tool?, J. Opt. Soc. Am. A Opt. Image Sci Vis., 2008, pp. 2088-2094, vol. 25.
P. J. Kelleret al., Life Sciences Require the Third Dimension, Curr. Opin. Cell. Biol., 2006, pp. 117-124, vol. 18.
K. Jeong et al., Functional Imaging in Photorefractive Tissue Speckle Holography, Opt. Comm., 2008, pp. 1860-1869, vol. 281.
K. Jeong et al., Multiple-Scattering Speckle in Holographic Optical Coherence Imaging, Appl. Phys. B, 2009, pp. 617-625, vol. 95.
J. D. Briers, Speckle fluctuations and biomedical optics: implications and applications, Optical Engineering, 1993, pp. 277-283, vol. 32.
International Preliminary Report on Patentability for PCT/US2011/040954, dated Dec. 19, 2012, 7 pages.
International Search Report and Written Opinion of the International Searching Authority for PCT/US2011/040954, dated Oct. 11, 2017, 8 pages.
International Preliminary Report on Patentability for PCT/US2009/036124, dated Sep. 7, 2010, 6 pages.
International Search Report and Written Opinion of the International Searching Authority for PCT/US2009/036124, dated Apr. 24, 2009, 7 pages.
D. Notle et al., Cellular Motility as a Novel Contrast Agent in Digital Holography of Tissue, Proceedings of SPIE, 2007, 11 pages.
K. Jeong et al. Fourier-Domain Holography in Photorefractive Quantum-Well Films, Applied Optics, Jul. 1, 2004, pp. 3802-3811, vol. 43, issue 19.
Lu et al., Low Sidelobe Limited Diffraction Optical Coherence Tomography, Proceedings of SPIE, 2002, pp. 300-311, vol. 4619.

\* cited by examiner

Tumor Tissue Preconditions

Fully-Proliferating Tumor

Hypoxic Core

Necrotic Core

Tumor Diameters approx. 400 – 500 microns

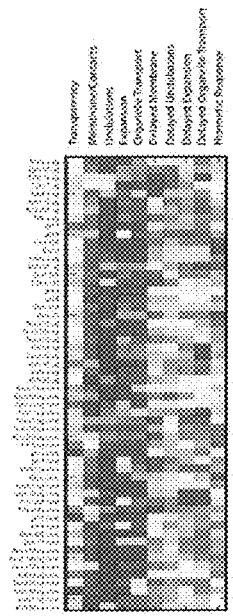
FIG. 11a
FIG. 11b
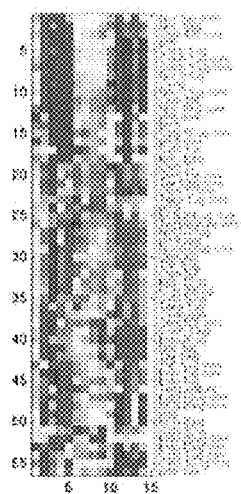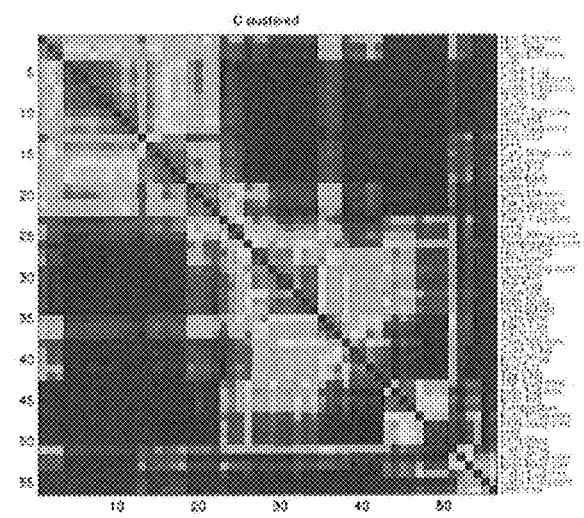
FIG. 12a
FIG. 12b

USING DIFFERENTIAL TIME-FREQUENCY TISSUE-RESPONSE SPECTROSCOPY TO EVALUATE LIVING BODY RESPONSE TO A DRUG

REFERENCE TO RELATED APPLICATIONS

This application is a continuation-in-part of and claims priority to co-pending application Ser. No. 12/874,855, filed on Sep. 2, 2010, and entitled "Method and Apparatus for Motility Contrast Imaging," which claims priority to PCT/US2009/036124 filed on Mar. 5, 2009, which further claims priority to U.S. provisional application No. 61/034,028, filed on Mar. 5, 2008. This application is also a continuation-in-part of and claims priority to co-pending application Ser. No. 13/704,464 filed on Dec. 14, 2012, and entitled "Digital Holographic Method of Measuring Cellular Activity and of Using Results to Screen Compounds," and claiming priority to PCT/US2011/040954, filed on Jun. 17, 2011, which claims priority to U.S. provisional application No. 61/397,885, filed on Jun. 17, 2010. This application is also a continuation-in-part of and claims priority to co-pending application Ser. No. 13/704,438 filed on Dec. 14, 2012, and claiming priority to PCT/US2011/040959, filed on Jun. 17, 2011, which claims priority to U.S. provisional application No. 61/397,885, filed on Jun. 17, 2010. The entire disclosure of the application Ser. Nos. 12/874,855; 13/704,438; and 13/704,464 are incorporated herein by reference.

STATEMENT OF GOVERNMENT INTEREST

This invention was made with government support under grant CBET 0756005 awarded by the National Science Foundation. The government has certain rights in the invention.

BACKGROUND

The present disclosure relates generally to the assessment of the health of living tissue and the profiling of the phenotypic response of tissue to perturbations, both environmental and pharmaceutical.

Cellular systems are highly complex, with high redundancy and dense cross-talk among signaling pathways. [1] (Note: Bracketed numbers refer to general reference publications listed at the end of the disclosure). Biochemical target-based high-content screening (HCS) can isolate single mechanisms in important pathways, but often fails to capture integrated system-wide responses. Phenotypic profiling, on the other hand, presents a systems-biology approach that has more biological relevance by capturing multimodal influence of therapeutics. [2] Although phenotypic profiling predates genomics that provided isolated targets, it remains today one of the most successful approaches for the discovery of new drugs. [3]

At present most phenotypic profiling is performed on two-dimensional culture, even though two-dimensional monolayer culture on flat hard surfaces does not respond to applied drugs in the same way as cells in their natural three-dimensional environment. This is in part because genomic profiles are not preserved in primary monolayer cultures. [4-6] There have been several comparative transcriptomic studies that have tracked the expression of genes associated with cell survival, proliferation, differentiation and resistance to therapy that are expressed differently in 2D cultures relative to three-dimensional culture. For example, three-dimensional culture from cell lines of epithelial ovarian cancer [7, 8], hepatocellular carcinoma [9-11] or colon cancer [12] display expression profiles more like those from tumor tissues than when grown in 2D. In addition, the three-dimensional environment of 3D culture presents different pharmacokinetics than 2D monolayer culture and produce differences in cancer drug sensitivities. [13-16]

An alternative approach to imaging form is to image function, and in particular functional motions. Motion is ubiquitous in all living things and occurs across broad spatial and temporal scales. At one extreme, motions of molecules during Brownian diffusion occur across nanometers at microsecond scales, while at the other extreme motions of metastatic crawling cells occur across millimeters taking many hours. As one spans these scales, many different functional processes are taking place: molecular diffusion, molecular polymerization or depolymerization of the cytoskeleton, segregation of enzymes into vesicles, exocytosis and endocytosis, shepherding of vesicles by molecular motors, active transport of mitochondria, cytoskeletal forces pushing and pulling on the nucleus, undulations of the cell membrane, cell-to-cell adhesions, deformation of the cell, cell division and ultimately to movement of individual cells through tissue. All of these very different types of cellular dynamics can be active and useful indicators of the functioning behavior of cells. The functional response of target cells to applied drugs is of particular relevance in drug screening.

Imaging motion in three-dimensional tissue is simpler than imaging structure or performing molecular imaging, because motion modulates coherent light through phase modulation. When light scatters from an object that is displacing, the phase of the light is modified. If the light has coherence, then the motion-induced phase shifts of one light path interfere with the phase shifts of other light paths in constructive and destructive interference. Even light that is multiply scattered in tissue carries a record of the different types of motions that the light encountered. By measuring the fluctuating phase of light scattered from living tissue, the different types of motion across the different space and time scales can be measured. The trade-off for greater depth of penetration into three-dimensional tissue is reduced spatial imaging resolution. But volumetric imaging of intracellular motions in tissue is still possible, within limits, by using low-coherence interferometry that can select light from specified depths by using coherence-gating approaches [17].

The 2D imaging techniques have been applied to drug screening and in particular to evaluating efficacy of a drug in disease treatment, such as anticancer drugs. Traditional 2D techniques can lead to false positives when a drug is more effective in 2D than in 3D, resulting in promising early drug leads that fail in animal models because the drug is more effective at killing tumor cells grown as monolayer cultures than as cells within multicellular tissues. An even greater impact is the false negative in drug screening in which a drug that would otherwise be effective in 3D yields a negative result at the 2D screening stage, thereby leading to the elimination of the drug. The end result of false positives and false negatives is that new drug discovery halves every nine years (in contrast to Moore's Law of the electronics industry in which chip capacity doubles every 18 months).

Phenotypic profiling can provide a significant advance in drug screening when based on 3D cultures. What is needed is a system and method for extracting high-content phenotypic responses from inside heterogeneous tissue and for accurately and meaningfully analyzing the resulting information to build a phenotype database to improve the efficiency of future drug screening.

SUMMARY

The present system and method relies upon feature recognition to segment the information in time-frequency tissue-response spectrograms to construct N-dimensional feature vectors. The feature vectors are used to generate a correlation matrix among a large number of different stimuli in the form of drugs, doses and conditions. Multi-dimensional scaling is applied to the correlation matrix to form a two-dimensional map of response relationships that retains rank distances from the higher-dimensionality feature matrix. The two-dimensional phenotypic profile space displays compact regions indicative of particular physiological responses, such as regions of enhanced active transport, membrane undulations and blebbing.

In a further attribute, the feature vectors can be used to generate feature masks against which new drugs and drug responses can be compared. A library of feature masks can be maintained and applied to the spectrogram of a new drug to find a corollary drug in the library that produces a similar physiological response.

DESCRIPTION OF THE FIGURES

The file of this patent contains at least one drawing executed in color. Copies of this patent with color drawings will be provided by the Office upon request and payment of the necessary fee.

FIGS. 9a and 9b are graphs corresponding to a morphometric analysis in which FIG. 9a is the raw differential spectrogram and FIG. 9b is the raw spectrogram modified according to a morphometric algorithm.

FIG. 11a is a spectrogram of feature vectors for 28 stimuli.

FIG. 11b is a similarity matrix for the feature vector spectrogram of FIG. 11a.

FIG. 12a is a spectrogram of feature vectors for 28 stimuli after unsupervised hierarchical clustering.

FIG. 12b is a similarity matrix for the feature vector spectrogram of FIG. 12a.

DETAILED DESCRIPTION

Figure 1:
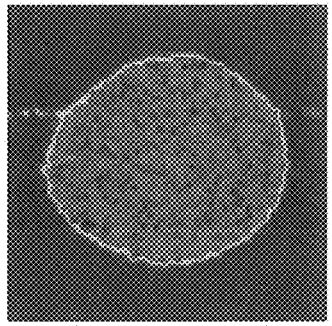
FIG. 1 includes motility contrast images of three nominal tumors, namely a fully proliferating tumor and tumors with a hypoxic and a necrotic core.
Figure 1:
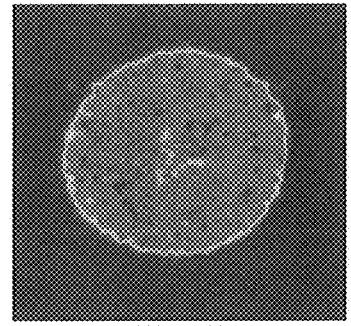
Figure 1:
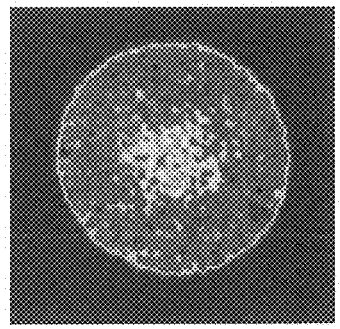

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention determines the internal health of living tissue by defining and monitoring internal states of health based on motility spectrograms that are used to classify phenotypic response of tissue to perturbations. In one aspect, the systems and methods of present disclosure utilize motility contrast imaging to map and evaluate cellular activity. In one embodiment, the imaging may be performed using the optical configuration disclosed in co-pending application Ser. No. 13/704,438, which is based on published PCT application WO 2011/160064 (the '064 Publication), or as disclosed in co-pending application Ser. No. 12/874,855, published as US2020/0331672, in which a depth-resolved holographic technique, namely holographic optical coherence imaging (OCI), is utilized to extract information concerning cellular and subcellular motion. The disclosure of the imaging systems and techniques in the published application Nos. US2020/0331672 and WO 2011/160064 are incorporated herein by reference.

The '064 Publication further describes the use of motility contrast imaging (MCI) to produce spectrogram responses of cell compounds. In particular, the '064 Publication describes extracting a spectrogram fingerprint of a differential response of a tissue sample in which a drug has been administered. The motility contrast images of several nominal tumors are shown in FIG. 1. The core can be strong proliferating (on the left) or strongly hypoxic (on the right), depending on the pre-condition of the tumor spheroids. When the core is hypoxic, it is ATP depleted and responds differently to stimuli, such as drugs or changing environmental conditions, than a healthy shell that has normal ATP levels.

The '064 Publication further discloses that a power spectrum in the frequency domain can be determined and more particularly changes in the power spectral density as a function of time through the shift in characteristic parameters are evaluated. The result is a differential spectrogram, such as the spectrograms shown in FIG. 2, which plots the differential relative spectral density for a given frequency at a time t relative to the initial time $t_0$. This differential spectrogram thus captures the changes in spectral content as a function of time after a dose, condition or other stimuli (or combination of stimuli) are applied to the target 3D body. The differential spectrogram is sensitive to shifts in the magnitudes of the spectral densities (dependent upon the number of moving constituents) and to shifts in the characteristic frequencies (i.e., the speed of the moving constituents).

Spectrogram Correlations

In one procedure, 28 different drugs, concentrations and conditions were applied to 28 different tumor spheroids, and spectrograms were obtained in each case using the imaging system and techniques described in the above-identified published applications. Table I below lists the different compounds, doses or conditions (hereinafter referred to as "stimuli") applied to the tumor spheroids, together with the expected physiological response.

TABLE I

Reference Compounds, Doses and Conditions

| Compound or Condition | Action |
| --- | --- |
| Temperature 24 to 37° C. | Increased motility |
| pH 6 | Weak acidic |
| KCN 20 µg/ml | Inhibit electron transport |
| Iodoacetate 1 µg/ml | Inhibits glycolysis |
| Osm 508 | Hypertonic cell desiccation |
| Osm 428 | Hypertonic cell desiccation |
| Iodoacetate 10 µg/ml | Inhibit glycolysis |
| KCN 200 µg/ml | Inhibit electron transport |
| TNF 5 µg/ml | Cytokine apoptosis induction |
| Cytochalasin 10 µg/ml | Anti-actin, anti-mitotic |
| Cytochalasin 1 µg/ml | Anti-actin, anti-mitotic |
| Iodoacetate 40 µg/ml | Inhibit glycolysis |
| pH 9 | Strong basic |
| Nocodazole 0.01 µg/ml | Anti-tubulin, anti-mitotic |
| Osm 154 | Strong Hypotonic cell swelling |
| Osm 77 | Strong Hypotonic cell swelling |
| Cytochalasin 50 µg/ml | Anti-actin, anti-mitotic, apoptosis |
| pH 5 | Strong acidic |
| Colchicine 10 µg/ml | Anti-tubulin, anti-mitotic |
| Iodoacetate 20 µg/ml | Inhibit glycolysis |
| Nocodazole 1 µg/ml | Anti-tubulin, anti-mitotic |
| Taxol 10 µg/ml | Tubulin stabilization, anti-mitotic |
| Cycloheximide | Apoptosis induction |
| Nocodazole 0.1 µg/ml | Anti-tubulin, anti-mitotic |
| Colchicine 1 µg/ml | Anti-tubulin, anti-mitotic |
| Nocodazole 10 µg/ml | Anti-tubulin, anti-mitotic |
| Taxol 1 µg/ml | Tubulin stabilization, anti-mitotic |
| pH 8 | Weak basic |

Figure 2:
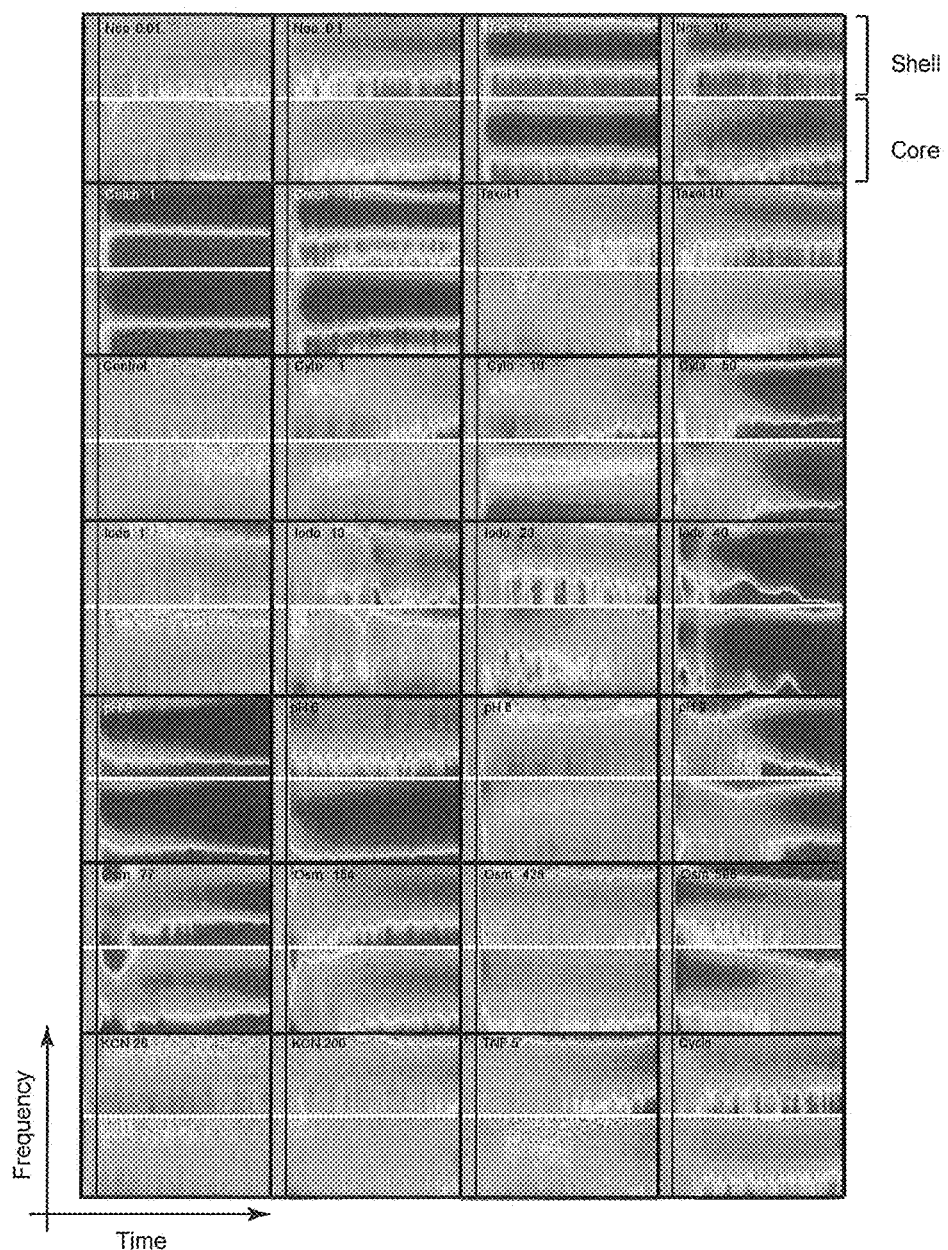
FIG. 2 includes the spectrograms for 28 different stimuli, namely drugs, doses and conditions.

The spectrograms for these drugs/stimuli are complex, showing many different types of features in response to the applied drugs. Similar drugs produced similar spectrograms, while widely differing spectrograms could be elicited from drugs with very different mechanisms of action. The spectrograms of the 28 different drugs/doses/conditions, separated by shell (top) and core (bottom), are shown in FIG. 2. For each spectrogram, frequency is along the vertical axis from 0.005 Hz to 5 Hz, while time is plotted along the horizontal axis corresponding to a duration of 6 hours after the dose or stimuli is applied. In the spectrograms of FIG. 2, increases in spectral density over the initial condition are represented by increasing shades of red while decreasing spectral density are represented by increasing shades of blue. For instance, for the drug/dose Nocodazole 0.01 µg/ml the spectral density shows a moderate increase over time at the low frequencies, while at the dose 0.1 µg/ml the increase is much more pronounced.

To initially capture the similarity or dissimilarity of the drug response spectrograms, a cross-correlation coefficient between spectrograms is calculated, as specified by:

$$C(x, y) = \frac{\sum_{v,t} S^{(x)}(v, t) S^{(y)}(v, t)}{\sqrt{\sum_{v,t} (S^{(x)}(v, t))^2} \sqrt{\sum_{v,t} (S^{(y)}(v, t))^2}}$$

where $S^{(x)}(v,t)$ is the spectrogram of drug/condition x, $S^{(y)}(v,t)$ is the spectrogram of drug/condition y and the sum is over both frequency and time. The correlation coefficient was calculated among the 28 conditions, treating the proliferating shell and the core of the tumor spheroid separately.

A similarity matrix provides the basis for a hierarchical clustering algorithm that can group different stimuli by their similar drug-response spectrograms. Each row of the N×N similarity matrix is an N-dimensional vector (where N corresponds to the number of compounds, doses and conditions applied to the tumor spheroid). The inner product of each row defines a measure of distance:

$$\text{Dist}(A, B) = \frac{1}{N} \sum_{y=1}^{N} C(A, y) C(B, y)$$

where C is the cross-correlation coefficient calculated above.

Inner products near unity correspond to "close" associations between stimuli, and inner products near negative unity correspond to "far" associations.

Figure 3:
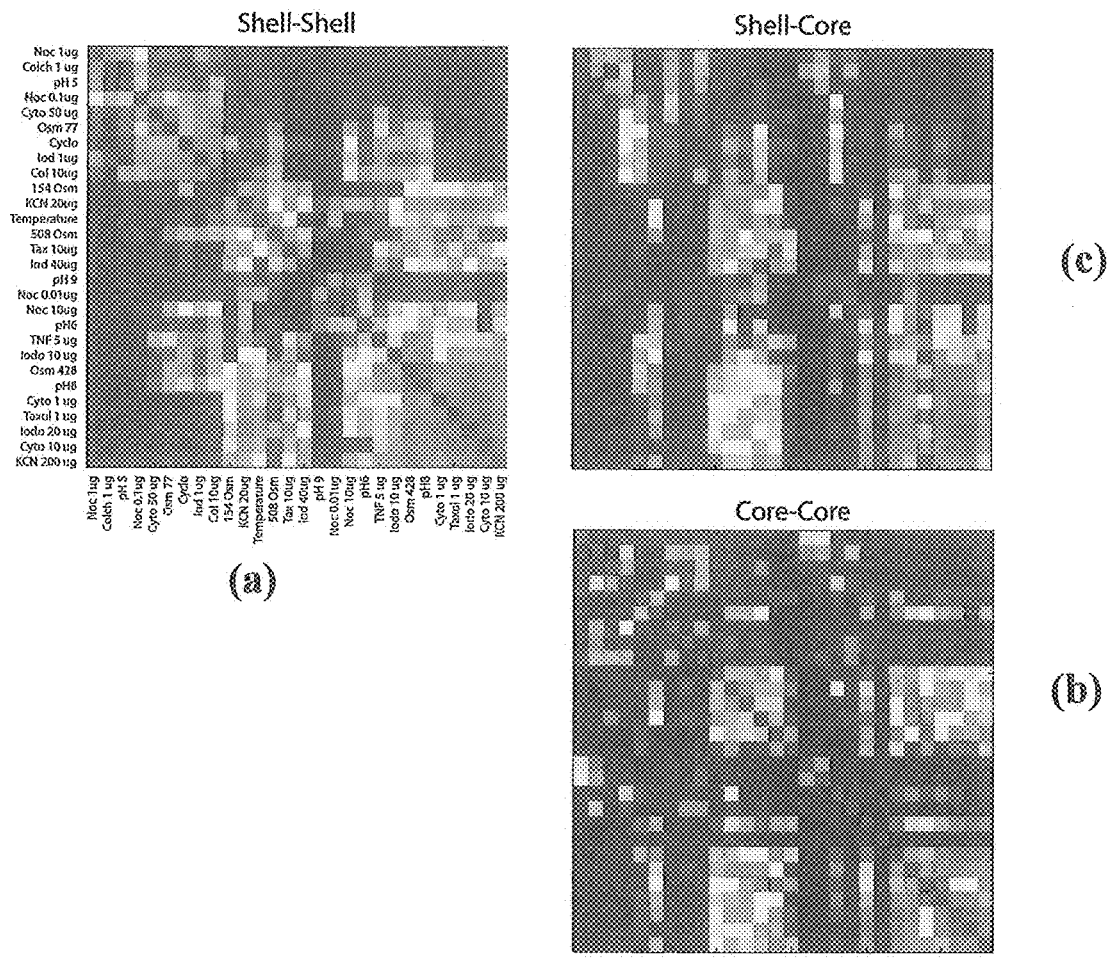
FIGS. 3a, 3b and 3c are similarity matrices for, respectively, shell-shell, core-core and shell-core correlations of the spectrograms of FIG. 2

The stimuli given in Table I can be grouped according to the hierarchical clustering of the drug responses based on the spectrograms of the proliferating shell. In a hierarchical clustering algorithm, at each stage the two closest vectors are identified and grouped into an average vector, and then the number of vectors decreases by one. The sequence of the vectors that are grouped in this way are retained until all vectors have been grouped. The sequential grouping of vectors produces a clustering of similar drug responses. The similarity matrix can be rearranged according to the sequence of grouping according to the shell-shell correlations with the result shown in upper left matrix of FIG. 3a. The similarity matrix shows structure with an approximately "block diagonal" appearance. If the matrix were truly block diagonal, the clustering would consist of groups of unique behaviors with no correlation between stimuli. However, in the case of the drug responses, there is considerable off-diagonal structure, which indicates that different groups of drug responses do share some aspects in common. Nevertheless, the drug response groupings exhibit "themes" of similar behavior. For instance, many of the anti-mitotic drugs, such as Nocodazole, Colchicine and Taxol, cluster in the bottom right of the figure, the cytochalasin and hypotonic osmolarity results are approximately in the middle, and the metabolic and hypertonic osmolarity responses are at the upper left.

The compounds were applied at multiple different doses, some below and some above EC50. Therefore, the clustering does not automatically group similar drugs together, but instead clusters responses. If a higher dose induces apoptosis, but a lower dose does not, then the higher dose will be grouped with other drugs or conditions that induce apoptosis. In an alternative analysis, each drug response can be referenced to its own EC50, which would remove the dose dependence in the clustering.

Multicellular tumor spheroids have different conditions for the proliferating shell relative to the core, which tends to be hypoxic and ATP depleted. Furthermore, large tumors (larger than 500 micron diameter) have increasingly necrotic cores. Tissue dynamics spectroscopy is volumetric (depth-gated) so the response of the (deeper) core can be compared to the different response of the (shallower) shell. The core-core correlations are shown in the lower right FIG. 3b for the same ordering as for the clustered data using the shell-shell correlations. There are many similarities in the core-core correlations, but with notable differences, and with several of the shell-shell blocks missing, such as the blocks in the upper right of the shell-shell matrix of FIG. 3a. The differences are because the shell and the core respond differently to the applied conditions. This is seen more clearly in upper right FIG. 3c which shows the correlation of the shell spectrograms with the core spectrograms. The diagonal elements of this similarity matrix are not all near unity, showing significant differences in the response of the core relative to the shell, even responding in the same tumor to the same conditions.

Figure 4:
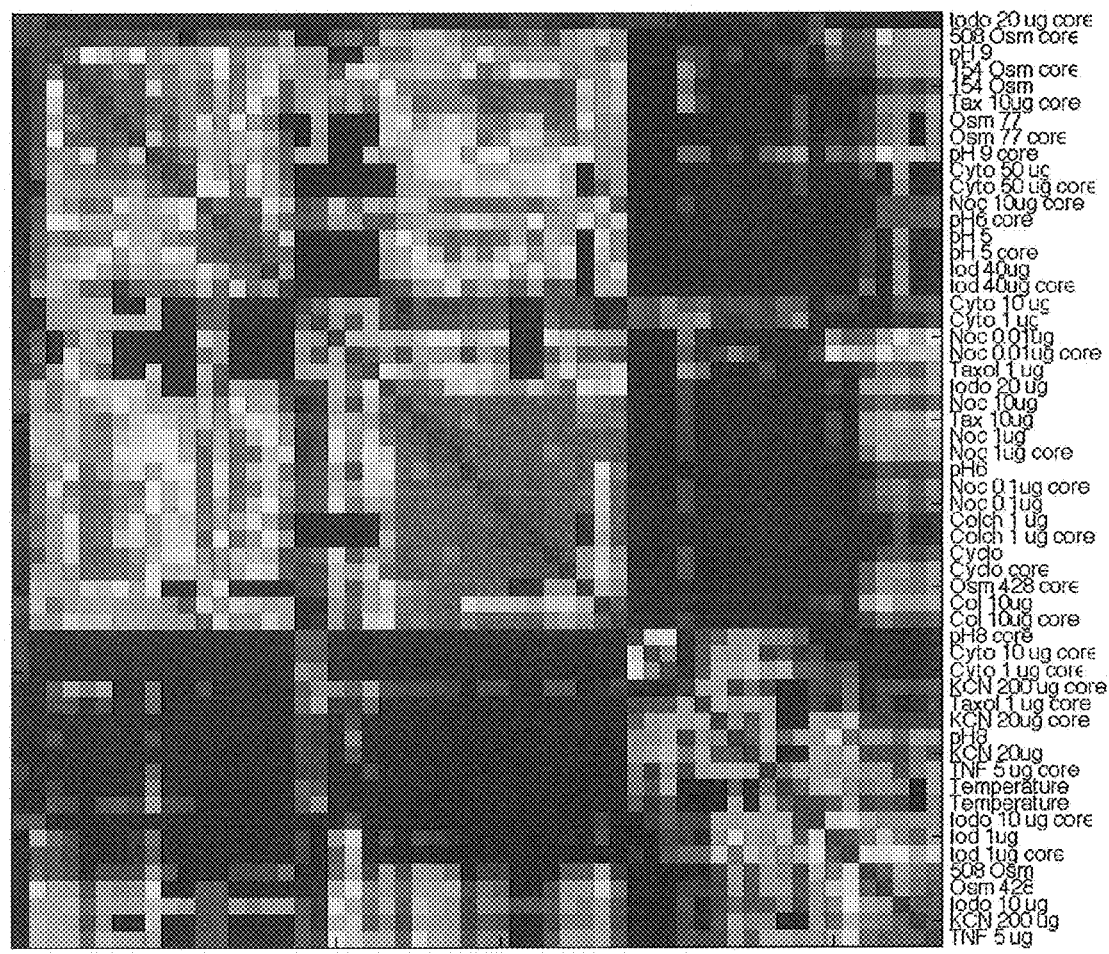
FIG. 4 is a clustered similarity matrix for the combination core and shell responses to 56 stimuli.

Because the core is under a different condition than the shell, the 28 conditions can be doubled to 56 conditions, which can be cross-correlated into a similarity matrix and clustered according to all 56 conditions. The resulting clustered similarity matrix is shown in FIG. 4. (Note that the stimuli applied to the core are so designated and the stimuli applied to the shell carry no separate identifier). Many of the shell and core spectrograms are clustered together (highly similar), but there are many other pairs that are separated in the clustering process because their respective spectrograms are not highly similar. This is likely a consequence of the ATP-depleted conditions of the core relative to the proliferating shell. For instance, an apoptotic response requires normal ATP concentrations and can occur in the shell, while the cells in the core would be forced to follow a necrotic path. This difference between apoptosis and necrosis based on ATP concentrations may be one of the differentiators between the spectrograms of the shell relative to the core. A more systematic study of these differences between the shell and the core may uncover specific spectrogram signatures for processes like apoptosis.

Motility Spectrograms and Cellular Dynamics

Figure 5:
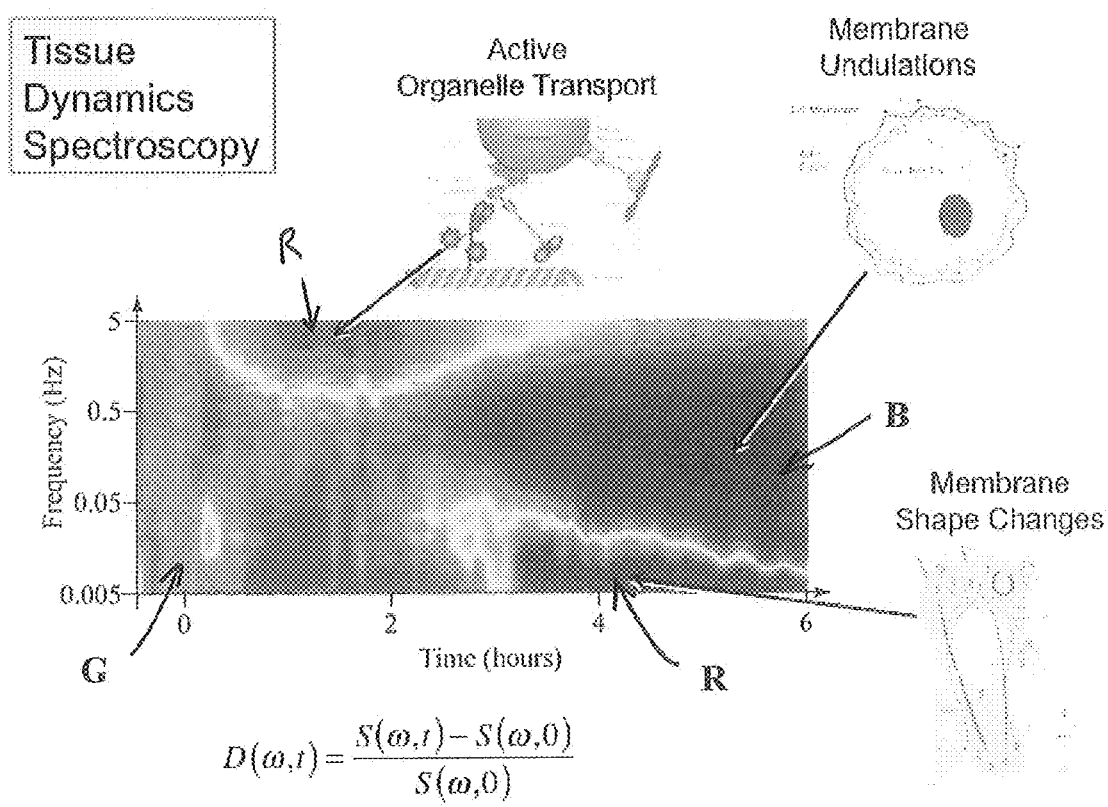
FIG. 5 is a map of spectral frequency responses corresponding to certain physiological responses of the tumor.

The information content of each spectrogram can be represented as feature maps that capture the signatures of the different drugs. These features can be related to physiological processes that occur inside the cells and generally in the tissue. For instance, the trend in the TDS (tissue dynamics spectroscopy) spectral frequencies are shown in FIG. 5 for motions of the organelles, membrane and general shape changes. The spectral frequency is along the y-axis and spans three decades of dynamic range, while time is along the x-axis. The baseline is set prior to t=0, and is used as the quantity in the denominator of spectral density equation for normalization. The change in the spectral content is plotted in false color, with Region R in deep red equal to 70% enhancement, and the Region B in deep blue equal to 70% inhibition. The intermediate Region G in green represents little or no change in spectral content. The response occurs in approximately three frequency bands that show distinctly different behavior: low-frequency (0.005 Hz to 0.1 Hz), mid-frequency (0.1 Hz to 1 Hz) and high-frequency (1 Hz to 5 Hz). The proliferating shell shows enhancements in the third frequency band after about an hour, while the core shows nearly an opposite response. At low frequencies, the shell is mostly unchanged until a strong onset at a much later time, while the core shows enhanced low frequencies for most of the duration of the experiment.

To interpret spectrograms, it is necessary to establish a correspondence of the frequencies observed in DLS (dynamic light scattering) with frequencies (and velocities and diffusion coefficients) obtained from the literature that are connected with specific biological targets and mechanisms. The lowest frequency in the experimental spectrograms described above is 0.005 Hz, and the highest frequency is 5 Hz. The general relationships for single backscattering under heterodyne (holographic) detection is given by: $q^2 D = \omega_D$ for diffusion, and $qv = \omega_d$ for directed transport, where D is the diffusion coefficient and v is a directed speed. The smallest and largest frequencies that can be captured in the experiments define the physical ranges for directed transport and diffusion, respectively, which are $0.006 < v < 2$ μm/sec, and $4 \times 10^{-4} < D < 0.1$ μm²/sec.

Figure 6:
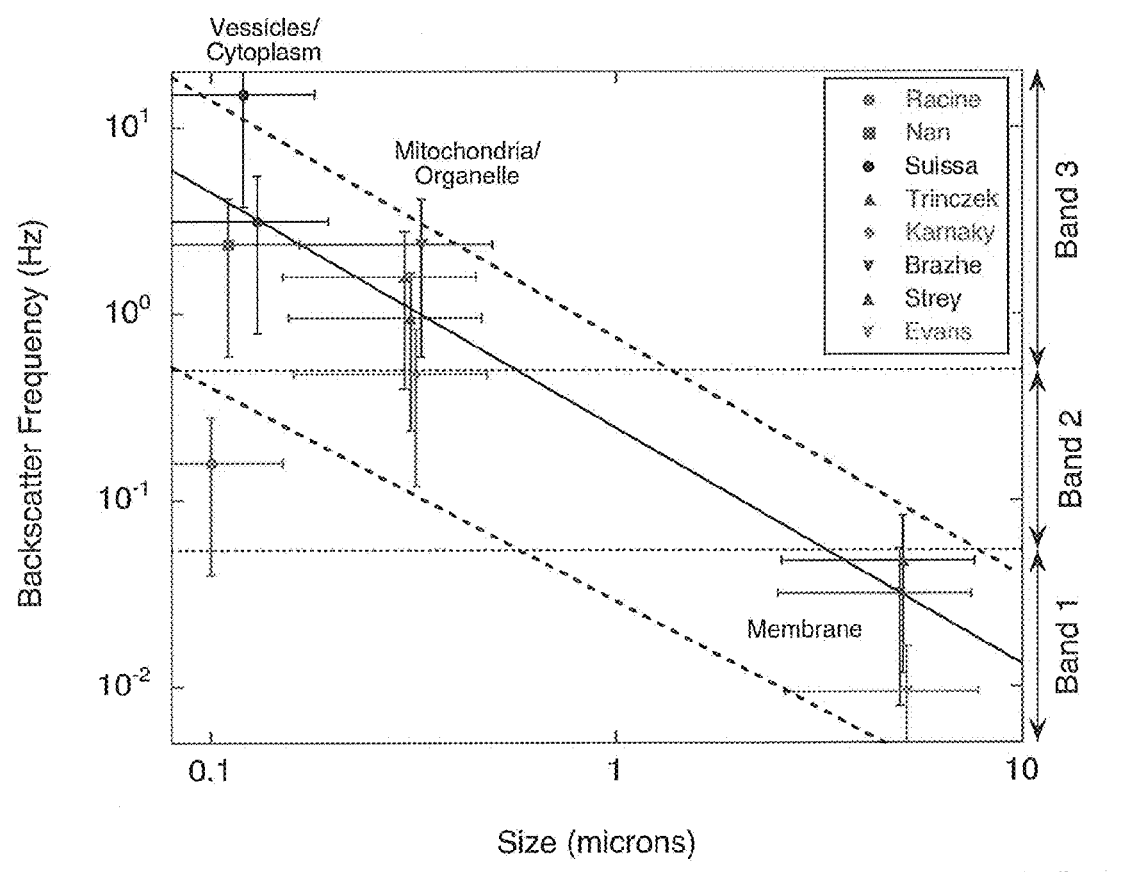
FIG. 6 is a graph of characteristic frequency (temporal scale) in relation to size (spatial scale) for certain physiological responses obtained from prior studies.

The velocity range is well within the range of intracellular motion in which molecular motors move organelles at speeds of microns per second [18-22]. Diffusion of very small organelles, as well as molecular diffusion, are too fast to be resolved by an expected maximum frame rate of 10 fps. Membrane undulations are a common feature of cellular motions, leading to the phenomenon of flicker [23-27]. The characteristic frequency for membrane undulations tends to be in the range around 0.01 to 0.1 Hz [21, 24, 28, 29]. Results from the literature are summarized in FIG. 6. The graph captures the general connection of spatial scale with temporal scale. Experiments on vesicles and the cytoplasm give the highest backscatter frequencies generally above 1 Hz and extending to tens of Hz. Larger mitochondria and organelles have slightly lower backscattering frequencies, but these are still in the range of the upper band frequencies of TDS shown in FIG. 5. Membrane motions are much slower, coinciding with the frequencies of the lower band in TDS. This spatial-temporal trend is only semi-quantitative, but it provides a general principle that may help disentangle the mixtures of frequencies that arise from multiple dynamic light scattering mechanisms.

Feature Masks

Figure 7:
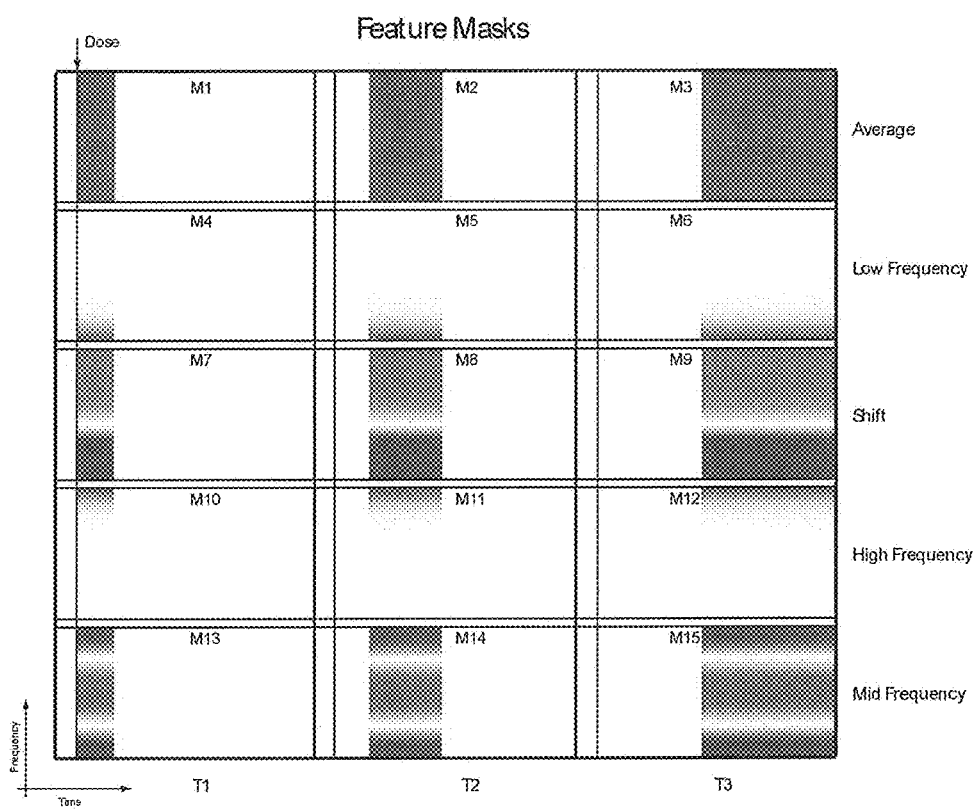
FIG. 7 includes feature masks generated from the feature vector of stimuli pH 9 obtained from the spectrogram of FIG. 2.

Therefore, there is a general trend of higher frequencies for smaller objects, and also trends in time with higher doses producing faster responses. These trends in frequency and time are captured by using feature masks that look at isolated regions of the frequency-time spectrogram. One embodiment of these feature masks is illustrated in FIG. 7.

The features used in the feature mask relate to a position in time and frequency on the spectrogram. For instance, a membrane undulation response is a mid-frequency response, while an organelle response is a high frequency response. Cell shape changes are low frequency. A hormetic response is a combined high/low frequency shift that occurs immediately upon application of the drug, but then decays quickly. All drug/condition spectrograms can be analyzed in terms of these features.

The drug-response spectrograms exhibit recognizable features that occur in characteristic frequency ranges at characteristic times after a dose is applied. Two approaches are applied to feature recognition and quantification of the drug-response spectrograms. One approach is based on projections of the spectrograms onto feature masks. There are many possible choices for feature masks, such as binary masks versus continuous-valued masks, local masks versus global masks, and orthonormal feature masks versus non-orthonormal. The time axis on the spectrograms primarily captures relaxation which is typically exponential. The frequency axis is the Fourier transform of the autocorrelation function, which also is typically exponentially correlated. Therefore, both the time and frequency axes are characterized by Laplace transforms for which there is no orthonormal basis. Therefore, an approach of matched filtering [30] can be used in which characteristic regions of the spectrograms can be interpreted mechanistically. For instance, it has been shown that low frequencies correspond to large-scale motion like blebbing or the formation of apoptotic bodies, while high frequencies correspond to membrane vesicles or internal organelle motions. [31] These processes and frequencies present natural frequency ranges within the data that are used to generate feature masks to extract these specific features.

Along the time axis, an increasing sampling for the feature masks is applied, sampling at short times (T1=0 to 50 minutes) for fast response, mid times (T2=50 to 150 minutes) for slower response and long times (T3=150 to 350 minutes) for long-term response. Along the frequency axis there are several characteristic frequencies that divide the response into natural frequency bands. These occur at 0.01 Hz (low), 0.1 Hz (mid) and 1 Hz (high). The resulting feature masks are shown in FIG. 7. The three time frames and five frequency signatures generate 15 feature masks. Masks M1-M3 capture the average spectral power change, masks M4-M6 capture low-frequency, masks M7-M9 measure the shift of the spectral weight to higher frequencies, masks M10-M12 capture high frequency motions, and masks M13-M15 capture enhanced mid frequencies.

In one rudimentary approach, overlaying a particular drug/dose spectrogram onto each of feature masks can reveal the expected response for the drug based on the feature mask or masks that generally correspond to the spectrogram. For instance overlaying the spectrogram of FIG. 5 onto the feature masks of FIG. 7 shows a general correspondence with mask M6 indicative of large scale motion of the cell and with M8 indicative of organelle transport that starts at a later time.

Figure 8A:
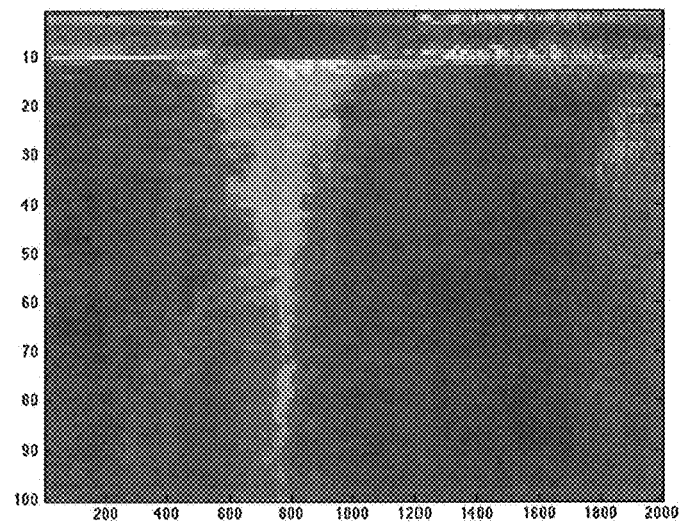
FIG. 8a is a spectrogram for a particular feature illustrating a frequency knee characteristic.
Figure 8B:
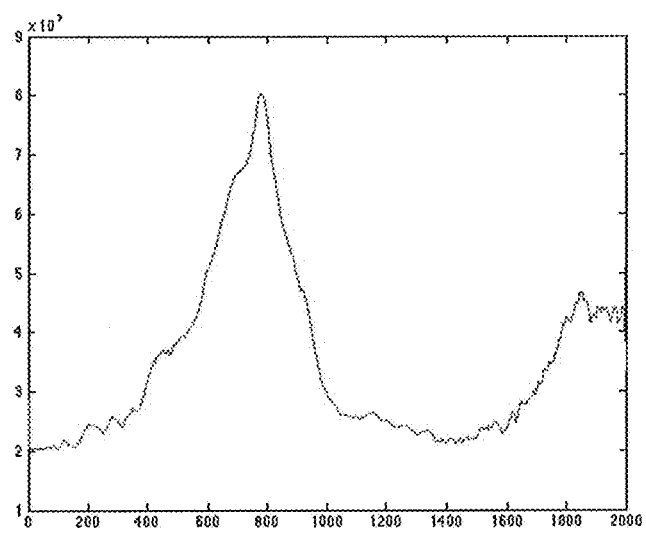
FIG. 8b is a plot of zero-crossings isolated from the spectrogram of FIG. 8a showing the knee frequency.

One important aspect of the time-frequency feature mask approach is the choice of frequency cutoffs for the different features. For instance, it is clear by assessing many of the spectrograms that there is a typical frequency knee, or edge, around 0.1 Hz. This frequency would be a natural frequency to define the boundary of a feature mask. To precisely establish this frequency, a level-set algorithm can be applied to an ensemble of many spectrograms from the same cell line responding to many different types of drugs. The level is set to the zero-crossings of the spectrogram. These zero-crossings are isolated in each of the spectrograms and then averaged. The result is shown in FIGS. 8(a)-8(b). There is a strong knee feature at a frequency around 0.1 Hz that is shared by most of the spectrograms. This becomes the bounding frequency of mid- or low-frequency masks. There is also a knee frequency around 1 Hz that defines the lower bound of the high-frequency mask that is associated with organelle transport.

Figure 9A:
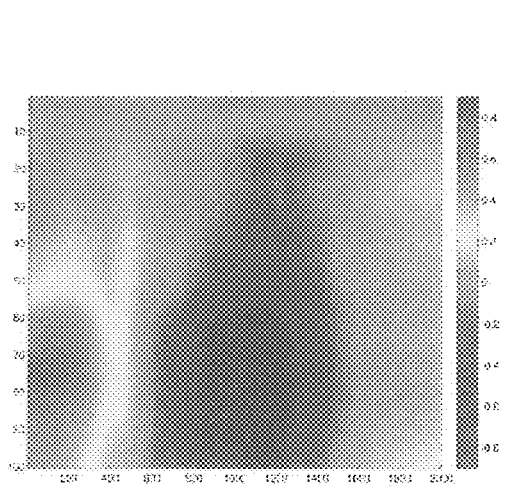
Figure 9B:
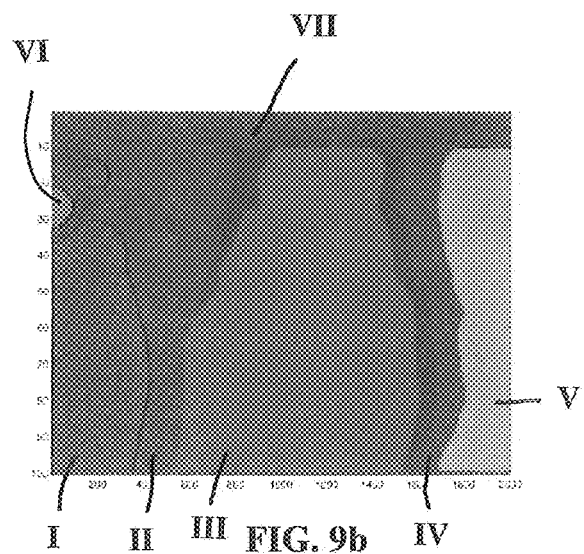

The second approach to feature extraction of spectrogram features is based on morphometric analysis. This analysis is based on the overall shape and position of certain features. An example of a morphometric analysis is shown in FIGS. 9a-9b for the mitochondrial toxin FCCP applied to a DLD-1 cell-line tumor spheroid. Time is the vertical axis, increasing downwards on a linear scale. The horizontal axis is frequency increasing to the right on a log scale. The drug is applied at t=10 on the vertical axis. The spectrogram in FIG. 9a is the raw differential spectrogram. This is used as the starting point of a morphometric algorithm that seeks broad areas of common response. The algorithm is based on percolation cluster labeling combined with level sets. The resulting identified regions are shown in FIG. 9b. There are 7 regions I-VII that were found in this case to be distinct. These regions become the masks that are applied to the spectrogram in FIG. 9a to extract the average values inside that time-frequency region. It is important to note that different spectrograms may differ quantitatively, but share common features. This morphometric approach can lead to feature vectors that are similar, while the more rigid approach to feature recognition described above might create feature vectors that are not highly similar because of frequency shifts between the two spectrograms. Therefore, the morphometric approach is considered to provide more robust comparisons of qualitatively similar features and hence more stable clustering results based on these feature vectors.

Feature Vectors

In one aspect of the present disclosure, each feature in the feature masks can be assigned a numerical value related to the strength and sign of the response for that feature in a particular spectrogram. The collection of feature values constitutes a feature vector. Therefore, each spectrogram has an associated feature vector.

The value of a feature is obtained by the inner product of the k-th feature mask $M_k(v,t)$ with the j-th differential spectrogram $D^j(v,t)$ $$V_k^j = \langle D^j(v,t), M_k(v,t) \rangle$$

that produces a k-dimensional vector component $V_k^j$ where j is the index for a condition (drug or dose or perturbation), and k is the index for a feature (time-frequency signature). The brackets denote the inner product through:

$$\langle D^j(v,t), M_k(v,t) \rangle = \frac{1}{N_{norm}} \sum_{p,q} D_{pq}^j M_{k,pq}$$

where the indexes p, q are along the frequency and time axes, respectively. The normalization $N_{norm}$ is $$N_{norm} = \sqrt{\sum_{p,q} M_{pq} M_{pq} \sum_{i,j} D_{pq} D_{pq}}$$

where $D_{pq}$ is taken only in the associated time region of the mask. This normalization captures the shape of features, but de-emphasizes the magnitude. This procedure is well suited to recognizing signature features and for clustering drug responses according to their features rather than the strength of their response.

Figure 10:
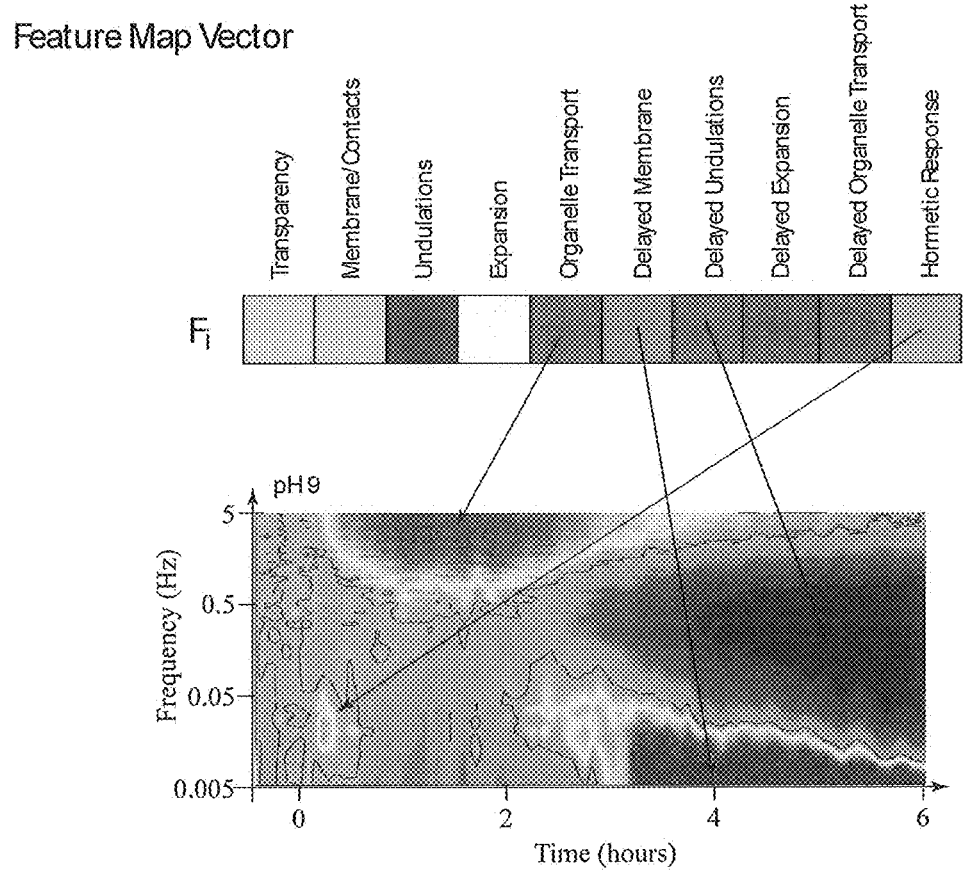
FIG. 10 shows a feature vector obtained from a spectrogram for the stimuli pH 9.

An example of a feature vector is shown in FIG. 10 associated with a spectrogram for pH 9. A collection of feature vectors for each of the 28 stimuli/conditions (see FIGS. 3a-c, FIG. 4), and including shell and core response separately, is shown in FIG. 11a. Each feature vector is like an N-dimensional vector. In the example of FIG. 11a, each drug or condition has a 10-dimensional vector that captures ten features of the spectrograms. There can be any number of dimensions, depending on the image masks that are generated to capture specific features. In this example, the key features include transparency, membrane/contacts, undulations, expansion, organelle transport, delayed membrane, delayed undulations, delayed expansion, delayed organelle transport and hormetic response. The strength of the responses are color-coded from red for a strong positive response to blue for a strong negative response.

Clustering

The similarity between two feature vectors for two different spectrograms is obtained as the inner, or dot, product between the two vectors. After the feature vectors are generated as shown in FIG. 11a, they are used to generate a similarity matrix among all the different drugs and conditions. The similarity of the i-th and j-th spectrogram is defined as the normalized correlation:

$$S^{ij} = \frac{\sum_k V_k^i V_k^j}{\sqrt{\sum_k V_k^i V_k^i \sum_k V_k^j V_k^j}}$$

where the similarity is normalized to unity when i=j. The feature vectors $V_k^j$ and the similarity matrix $S^{ij}$ for the 28 doses and conditions of Table I above, plus two negative controls, are shown in FIGS. 11a-b. In these figures, the proliferating shell and the core are treated independently, leading to 60 feature vectors and a 60×60 similarity matrix. The similarity matrix in the present example is shown in FIG. 11b and is unity along the main diagonal. The ordering in FIG. 11b is by drug and dose, with the shell alternating with the core. While there is some clustering of similarities, the similarity matrix and feature vectors do not show strong clustering, except for the tubulin destabilizing compounds that share many features in common.

Despite the grouping of increasing doses of some drugs (e. g., Nocodazole, Iodoacetate, cytochalasin, etc.), there is little structure to the matrix in FIG. 11b so the informational content is of little value in drug screening. One of the goals of phenotypic profiling is to re-order the similarity matrix to group common drug responses together. There is no unique way to order similarity, and there are several common algorithms that lead to similar, but not identical, orderings. One known approach is unsupervised hierarchical clustering. [32] (See another example in "Unsupervised Hierarchical Clustering via a Genetic Algorithm", William A. Greene (Proc. IEEE Cong. Evol. Comput., Canberra, Australia, 2003, pp. 998-1005), the entire disclosure of which is incorporated herein by reference). This is an iterative process that sequentially groups pairs of similar responses to produce tree structures. Unsupervised ordering has the advantage that no predefined structures or substructures are defined for the process, leading to an objective grouping of similar responses.

The similarity matrix and feature vectors after unsupervised hierarchical clustering according to "distance" are shown in FIG. 12a-12b. In comparing the "non-clustered" similarity matrix of FIG. 11b with the matrix of FIG. 12b it can be seen that the latter similarity matrix is nearly block-diagonal in which similar spectrograms are grouped together, with low cross-talk among the groups. The feature vectors are also grouped in FIG. 12a, showing groups of spectrograms that share features in common. The selected features have putative physiological interpretations (such as blebbing, undulations and organelle motions)[31], so the groupings of features also group the physiological responses into a phenotypic profile for these standard compounds and conditions.

It can thus be appreciated that the clustered similarity matrix of FIG. 12b is higher in information content than the similarity matrix of FIG. 11b, and therefore more useful in screening a new drug. In one aspect, the spectrogram of a new drug/dose/stimuli can be reduced to a feature vector, as explained above, and then combined with feature vectors of known drug/dose/stimuli, in the manner of the feature vector matrix of FIG. 11a, and ultimately incorporated into a similarity matrix, such as the matrix of FIG. 11b. After clustering a clustered similarity matrix such as the matrix of FIG. 12b can be used to identify the group in which the new drug/dose/stimuli resides. The new drug can then be expected to produce the physiological responses of that group.

There are several aspects to note in the ordered list of the vector in FIG. 12a. In general, similar compound classes are clustered together, such as the anti-tubulin drugs Nocodazole and Colchicine. But these compounds cluster separately from Taxol which is a tubulin stabilizing drug. In addition, similar environmental conditions cluster together, such as hypotonic osmolarity and low pH separately from hypertonic osmolarity and high pH. One aspect that is striking in its absence is the low correlation between the shell and the core response of the same tumor spheroid to the same compound or condition. This phenotypic difference between the shell and the core of a single spheroid is discussed in more detail herein.

Multidimensional Scaling

The disadvantage of hierarchical clustering is that it produces a linear arrangement that does not faithfully represent distance between nodes (in which a node corresponds to a drug/dose/stimuli). In addition, it is an ordering algorithm rather than a clustering algorithm. [33] To test the results of hierarchical clustering, a k-means clustering and level-set clustering can be applied on the raw similarity matrix in FIG. 4. The resulting ordering of the drugs and conditions change in detail, but the overall groupings and block-diagonal structure of the reordered similarity matrix remain nearly the same with respect to the similarity matrix shown in FIG. 12b. However, none of these ordering or clustering algorithms faithfully represent the distance relationships that are contained within the original similarity matrix. As subclusters are combined into larger clusters, especially in hierarchical clustering, it is possible to have two adjacent nodes that have very low similarity and hence should be far apart. The final ordering is linear, and distance relationships are not represented.

Figure 13:
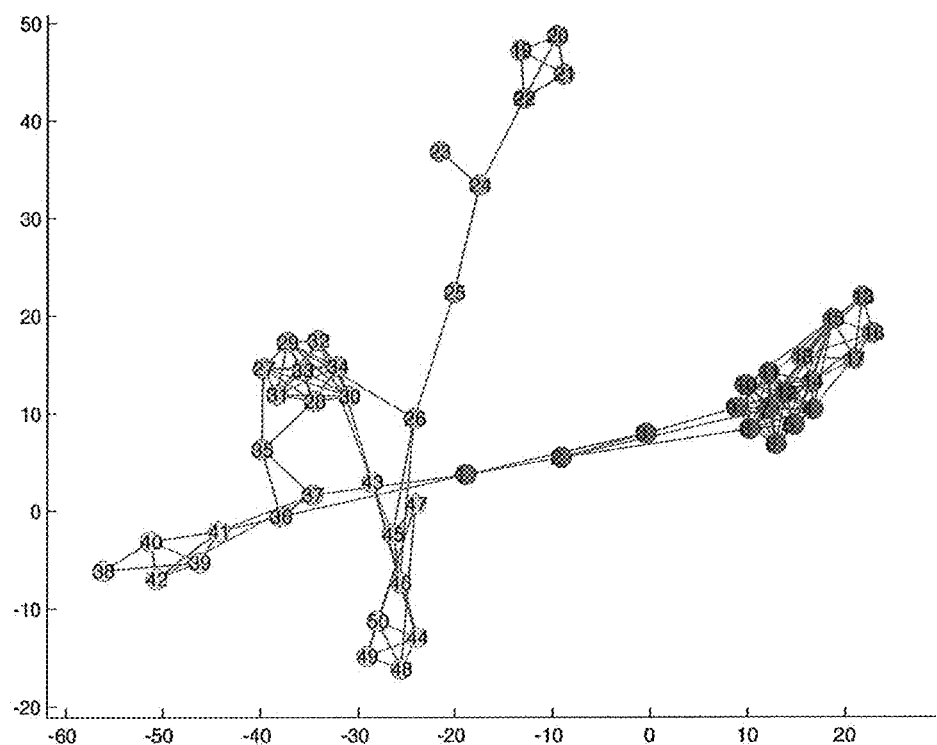
FIG. 13 is a network diagram of illustrating strong similarities among multiple stimuli.

As one solution to this "distance" problem, the groups of clustered cases can be converted to a network diagram, as shown in FIG. 13. Each numbered node represents a particular stimuli (i.e., compound, drug or condition). Strong similarity is denoted by a line connecting two nodes. Close proximity of nodes signifies similar phenotypic response. The network diagram of FIG. 13 provides a clear visual indication of groupings according to phenotypic response that can be useful in drug screening.

A more quantitative solution to this "distance" problem is provided by multidimensional scaling (MDS). [32] In multidimensional scaling, a low-dimensional representation is sought in which similar response nodes are placed close to one another and dissimilar response nodes are placed far apart. The spatial near-far relationships in a low-dimensional graph preserve the high-dimensional near-far relationships of the original feature vectors. Multidimensional scaling is not a "projection" to a lower dimensional plane, but is instead a one-to-one mapping that retains ordering of distances. As with all data compression the actual metric distances are lost in the process; however, the general relationships of nearness or similarity are preserved.

To apply multidimensional scaling to a similarity matrix, such as the matrix of FIG. 4, a distance matrix is defined as $d^{ij}=1-S^{ij}$. The MDS algorithm assigns a cost function that is to be minimized. The cost function is the difference between the distance of the two-dimensional location of nodes and the distance defined from the similarity matrix. The cost function is:

$$C = \sum_{j>i} (|r_i - r_j| - d_{ij})^2$$

where $r_i$ is a vector in the low-dimensional target space. Using a simple Euclidean distance norm this cost function is minimized using simulated annealing [34], starting from a set of initial positions in two dimensions determined by the first two principal components from principal component analysis. [32] (Examples are also shown in "Pairwise data clustering by deterministic annealing", T. Hofmann, J. M. Buhmann, Pattern Analysis and Machine Intelligence, IEEE Transactions, Vol. 19, no. 1, pp. 1-14, January 1997; and "Multidimensional Scaling by Deterministic Annealing," H. Klock, J. Buhmann, Proc. Int'l Workshop Energy Minimization Methods in Computer Vision and Pattern Recognition, pp. 245-260, 197; both disclosures of which are incorporated herein by reference). The simulated annealing proceeds through 1000 iterations, with a 0.1% decrease in effective temperature at each iteration. The final positions that emerge from the MDS algorithm appear in the low-dimensional space in a pattern that preserves the trend of distances $d_{ij}$ from the high-dimensional space spanned by the feature vectors.

Figure 14:
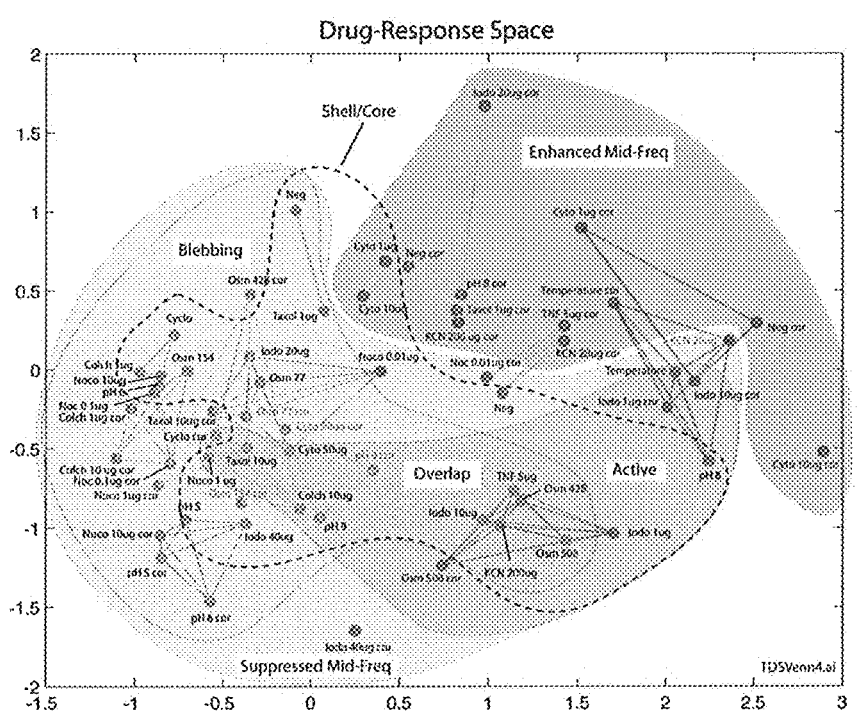
FIG. 14 is a Venn diagram generated by multi-dimensional scaling of the spectrogram of FIG. 12.

The results of multidimensional scaling of the data in FIG. 12 are shown in FIG. 14. This low-dimensional phenotypic space has two dimensions. The axes do not have direct physical meaning, but the distribution of nodes retains the ordering of distances that occur in the similarity matrix of FIG. 12. Similar drug responses are grouped closely, and far from other unrelated drug responses. Because of this spatial grouping and separation, it is possible to draw a Venn diagram based on the physiological features in the feature vectors. The Venn diagram of FIG. 14 shows the drug responses with enhanced mid-frequency (membrane undulations), enhanced low frequency (shape changes and blebbing) and enhanced high frequency/active (vesicle and organelle transport). The network connections drawn on the figure are from k-means clustering and show local clusters. The dashed line shows a separation between core response (outside the line) and shell response (inside the line). There are exceptions in this shell-core separation for hypotonic osmolarity, high pH and high-dosage cytochalasin, but in general the shell responses lie closer together near the center of the phenotypic space than the outlying core responses.

An interesting region is the overlap between blebbing and active organelle/vesicle transport. Taken together, these may be expected if there is apoptosis during which apoptotic bodies are separated from the main cell, and active organelle transport drives the cellular decomposition. There are no drug responses in this overlap region from the hypoxic core which is ATP depleted and cannot support apoptosis.

It can be seen that the information content of the map of FIG. 14 far exceeds the content of the original similarity matrix of FIG. 4. The map resulting from the multidimensional scaling can be easily used to identify similar physiological responses among drugs and more importantly to identify expected physiological responses of new drugs being screened. It can be appreciated that the all of the steps leading from the original spectrogram for a new drug to the map of FIG. 14 can be performed with software.

Figure 15:
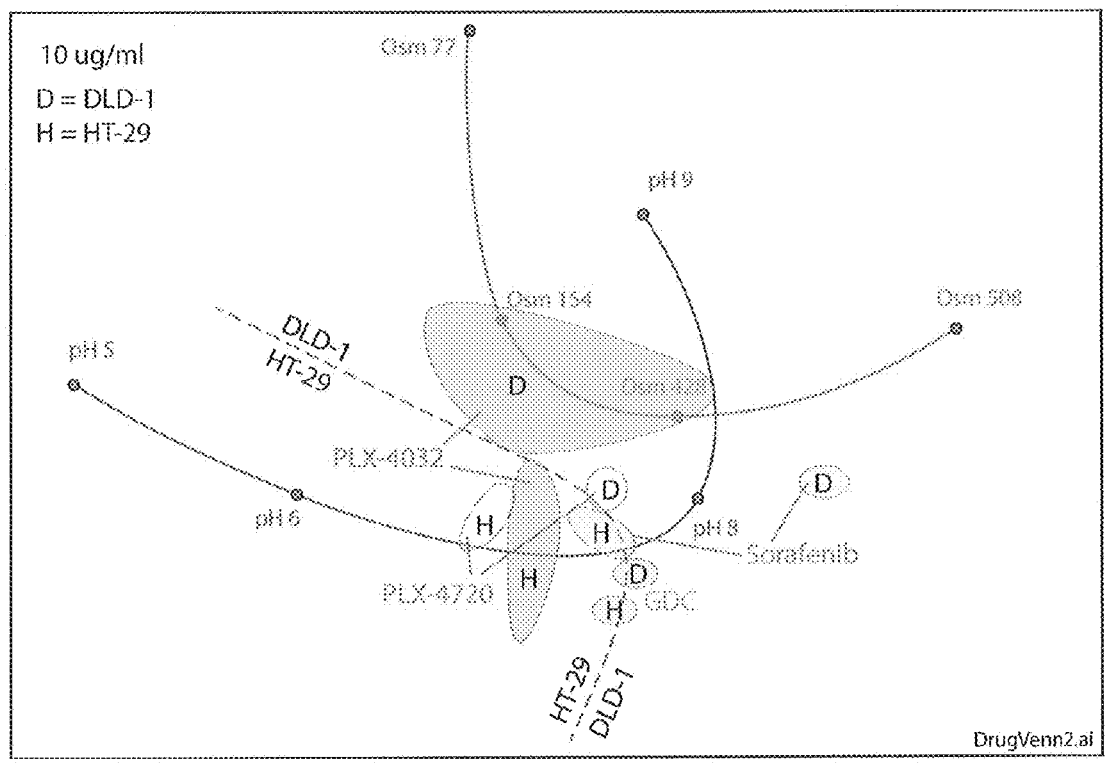
FIG. 15 is a diagram showing trajectories of pH and osmolarity in a MDS space of several Raf inhibitors acting on adenocarcinomas DLD-1 and HT-29.

Former applications of multidimensional scaling have had the drawback that the axes do not relate to physically meaningful quantities. However, the application of specific conditions to living tissues can be performed with conditions that have continuously variable values that are continuously tuned through normal physiological conditions. By including these data in the multidimensional scaling, one obtains a so-called trajectory for that condition through the MDS space. One example of such a condition is the pH of the culture medium that can be tuned from pH=5 to pH=9 passing through physiological normal pH=7.3. Another example is the osmolarity that can be tuned from 150 mOsm through physiological 300 mOsm to 450 mOsm. Examples of these trajectories on the MDS phenotypic profile of a group of Raf inhibitors is shown in FIG. 15. The pH and osmolarity data define trajectories through the MDS space. These trajectories enable the axes of the MDS space to acquire physiological meaning in relation to the drug responses.

Proliferating Shell and Hypoxic Core Phenotypes

As an example of phenotypic profiling based on hypoxic phenotypes, multicellular tumor spheroids provide a natural format to study phenotypic differences in the drug response between normoxic and hypoxic tissue. When tumor spheroids have a diameter larger than approximately 400 microns, the transport of oxygen into the core of the spheroid is impeded, resulting in hypoxic tissue and a band of quiescent cells inside the outer shell of proliferating cells. [35] There is evidence that the phenomenon of multicellular resistance to anticancer drugs displayed by avascular solid tumors is caused, in part, by the population of quiescent cells. [36, 37] In addition, hypoxia is a factor in oncogenic progression [38, 39] and may participate in the epithelial to mesenchymal transition that ultimately leads to metastasis. [40-43] For these reasons, comparing the effect of anticancer drugs on the hypoxic core relative to the quiescent or proliferating shells may shed light on multicellular resistance.

Figure 16:
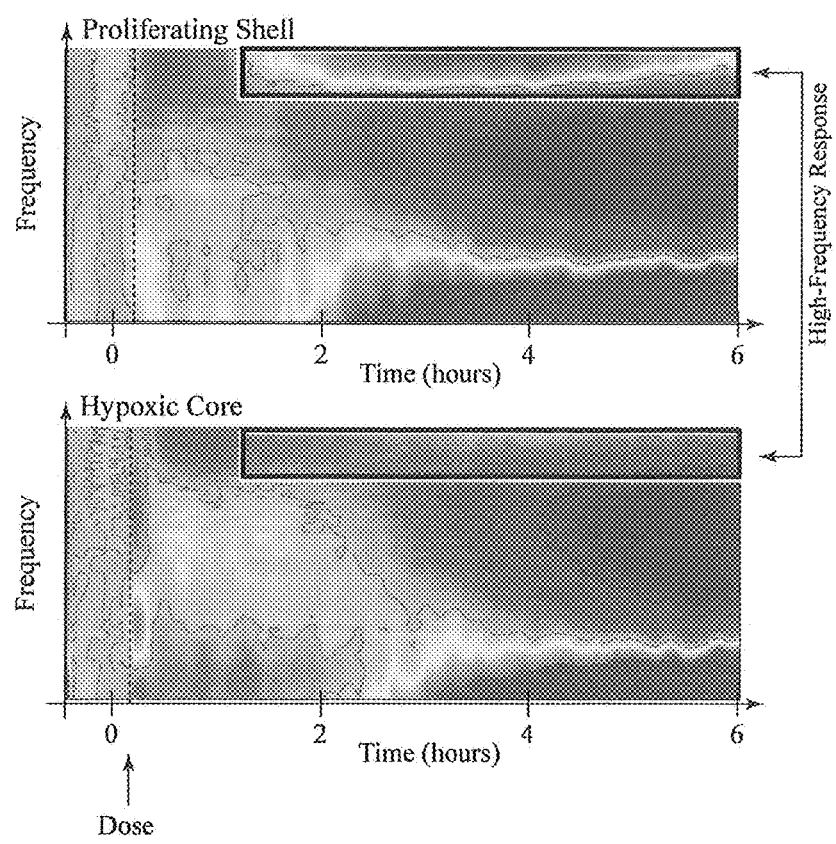
FIG. 16 includes spectrograms of a proliferating shell and hypoxic core of a tumor responding to particular stimuli, namely cytochalasin D at 50 µg/ml.

An understanding of the shell-core differences can be gained by analyzing the shell and core spectrograms responding to cytochalasin D at 50 µg/ml shown in FIG. 16. The core spectrogram at the bottom of FIG. 16 shows an initially strong mid-frequency enhancement (shortly after time 0) caused by the weakening of the actin cortex that reduces the stiffness of the cell membrane. After two hours, there is a strong onset of low-frequency enhancement for both the shell and the core. However, the shell, shown in the top spectrogram in FIG. 16, shows a strong enhancement of the high-frequencies (starting just before two hours) associated with vesicle and organelle transport that is missing in the core spectrogram response. This represents a significant physiological difference in the role of the drug for normoxic vs. hypoxic tissue. Based on the physiological processes of apoptosis (active transport requiring ATP and hence normal oxygen levels) relative to necrosis (passive degradation of the cell without need for ATP), this phenotypic difference can be tentatively ascribed to apoptosis in the shell as opposed to necrosis in the core. This assignment of high-frequency fluctuations associated with apoptosis is consistent with decorrelation times measured using OCT in vitro [44], and is also supported by confocal two-photon microscopy of these drugs on spheroids of these cell types.

The active transport that is present in the shell but missing in the core, combined with the presence of low-frequency enhancement that is common to both, suggests a metric that is the logical AND of both of the features to create an "apoptotic" index that quantitatively captures this feature. This index is constructed from the feature masks appropriate to the low- and high-frequency features, which are masks M6 and M12 of FIG. 7. The apoptotic index can be defined by:

$$M^i = \text{sqrt}(V_6^i)\text{sqrt}(V_{12}^i)$$

$$A^i = Re\{M^i\} - Im\{M^i\}$$

in which $V_6^i$ and $V_{12}^i$ are the feature vector values for masks M6 and M12 (determined as discussed above). The difference between the real and the imaginary parts generates the logical AND with positive apoptotic indexes only for features that themselves are both positive.

Figure 17A:
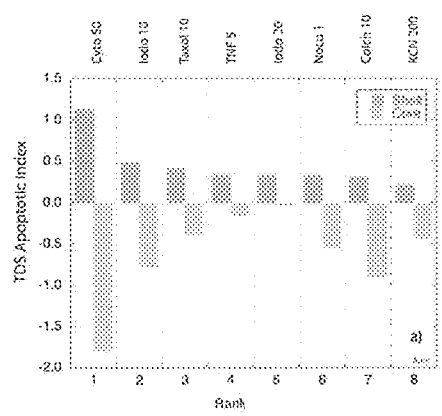
FIG. 17a is a graph of apoptotic indexes for the shell and core of a tumor responding to eight stimuli.

The apoptotic index was calculated for the shell and the core spectrograms and ranked in decreasing order by the shell. The apoptotic index of the shell response for the top eight apoptotic indexes is shown in FIG. 17a above the zero line. The strongest apoptotic index is for the shell responding to cytochalasin at 50 µg/ml. Also shown in FIG. 17a below the zero line are the corresponding apoptotic indexes for the core responses in each case. For this set of 8 drug doses, that produced the strongest positive apoptotic indexes in the shell, the apoptotic index of the cores are all negative. In the cases when the shell has strong active transport in addition to strong low-frequency enhancements, the core is missing one or the other of these features. Upon closer inspection, the missing feature is the active transport band at high frequency in all cases. The key physiological aspect of the core is the lack of ATP to drive active processes, such as the formation of sequestering vesicles and apoptotic bodies. The negative apoptotic indexes of the core region for each of these drugs reflects the quiescent/hypoxic resistance of solid tumors to anti-cancer drugs. For instance, the anti-actin anti-mitotic drug cytochalasin D shows the strongest apoptotic index for the shell, but the strongest negative mitotic index for the core. Taxol and Colchicine also show strong differences in the apoptotic index between the shell and the core.

Figure 17B:
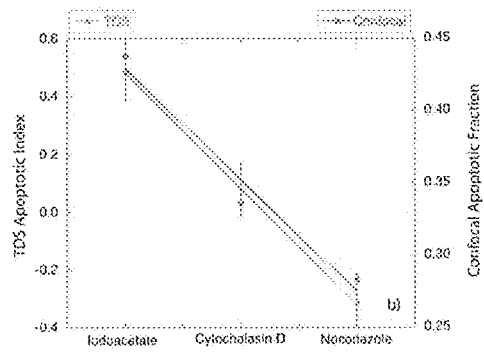
FIG. 17b is graph comparing data for three stimuli obtained from the tissue dynamic spectroscopy described herein and prior art data.

The independent validation for apoptotic processes to confirm their participation in the drug response was obtained through a series of multiphoton confocal microscopy experiments carried out using the UMR-106 spheroids. Spheroids were cultured at 37° C. in the presence of 10 µg/mL cytochalasin D, paclitaxel, and Colchicine for 4 hours and Iodoacetate for 3 hours. The live, apoptotic, and dead cells in the spheroid outer shell were visualized by optical section using a 20× water immersion objective up to a depth of 100 µm using Hoechst 33342 (live), Yo-Pro-1 (apoptotic), and propidium iodide (dead) (Invitrogen, Grand Island, N.Y.) vital dyes on a Nikon AIR multiphoton microscope with Mai Tai DeepSee tunable IR laser at 750 nm. The percentage of live, apoptotic, and dead cells in the spheroid outer shell was determined for six different spheroids. The results for Nocodazole, cytochalasin and Iodoacetate, all at 10 µg/ml, correspond to the upper line in the graph of FIG. 17b. The data are ranked by decreasing apoptotic ratio. These data show that Nocodazole, cytochalasin and Iodoacetate all induce an apoptotic response in the tumor spheroids. The strongest apoptotic response is for 10 µg/ml Iodoacetate, which has the strongest apoptotic index in FIG. 17b. The bottom line in the graph of FIG. 17b shows the corresponding data for the tissue dynamic spectroscopy shown in FIG. 17a.

Information Content of TDS

A key question about the drug-response spectrograms is how much information is contained in these data structures. There are many types of intracellular motions, including organelle transport, endo- and exocytosis, membrane undulations, cytoplasmic streaming, cytoskeletal rearrangements, force relaxation and shape changes, among others. While general trends in the spectrograms are understood in terms of these types of motion, it needs to be established how much information can be obtained from tissue dynamics spectroscopy.

Information can be measured in terms of Shannon entropy. For a probability distribution p(x), the Shannon entropy is defined as:

$$H(x) = -\sum_i p(x_i) \log p(x_i)$$

Figure 18:
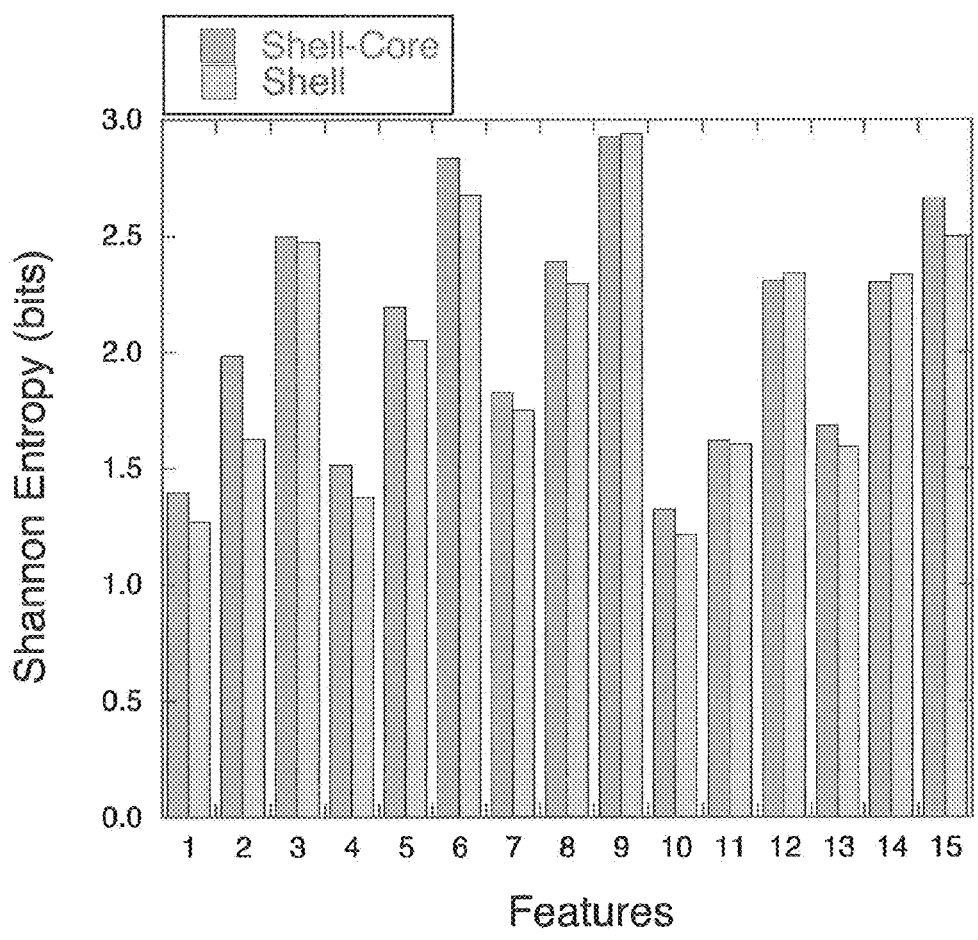
FIG. 18 is a graph of entropy data for fourteen feature vectors.

The probability distribution for the feature vectors of phenotypic profiling by tissue dynamics spectroscopy is obtained as the histogram of the values among the individual features. The entropy for the data in FIGS. 12a-12b is shown in FIG. 18 for the fifteen features comparing the shell and core responses versus shell alone. The horizontal axis corresponds to the 15 features while the vertical axis represents the Shannon entropy value, which if applied to the feature vectors identifies how much information is obtained from the vectors. The entropy values for shell and core feature vectors are all moderately higher than for only shell feature vectors. The average entropy per channel is approximately two bits.

An important aspect of information analysis of a data structure like a drug-response spectrogram is the definition of joint and mutual entropies for joint probability distributions. These entropy measures arise when there is shared information among numerous channels. For instance, for two channels, the joint entropy is:

$$J(x, y) = -\sum_{ij} p(x_i, y_j) \log p(x_i, y_j)$$

and the mutual entropy is:

$$M(x, y) = \sum_{ij} p(x_i, y_j) \log \frac{p(x_i, y_j)}{p(x_i)p(y_j)}$$

$$= H(x) + H(y) - J(x, y)$$

where $p(x_i, y_j)$ is the joint probability of two variables. The mutual entropy is equal to zero for independent variables, while $M(x,y) = H(x) = H(y)$ for linearly dependent variables.

Similarly, J(x,y)=H(x)+H(y) for independent variables, and J(x,y)=H(x)=H(y) for linearly dependent variables. In other words, when there are two channels that have perfect correlation, the total information content is simply the information content of a single channel.

Figure 19A:
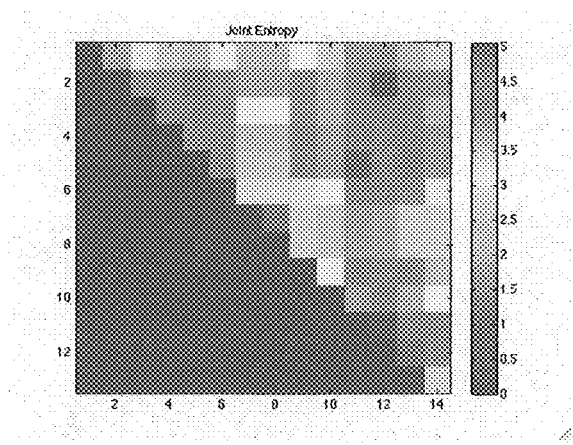
FIGS. 19a and 19b are maps of two-variable joint and mutual entropies for the fourteen feature vectors shown in FIG. 18.
Figure 19B:
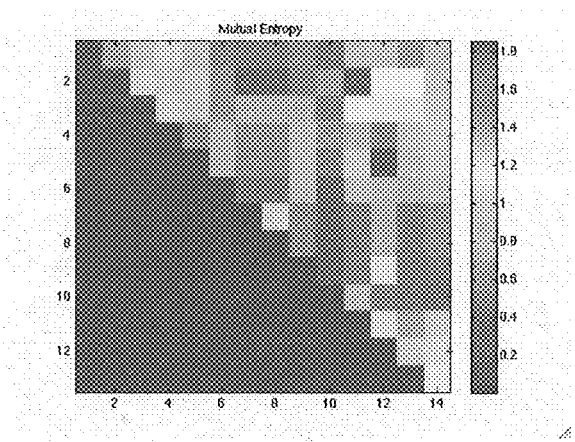

Examples of two-variable joint and mutual entropies are plotted in FIGS. 19a and 19b for the fourteen features of the 60 drugs, doses and conditions of the spectrograms of FIGS. 12a-12b. From the mutual entropy figure, there are cases of strong mutual information content among some pairs of channels, for instance channel 11 and channel 2 share almost 2 bits of information. (See, FIG. 19b).

The joint entropy among three channels is:

$$J(x, y, z) = -\sum_{ijk} p(x_i, y_j, z_k) \log p(x_i, y_j, z_k)$$

and by extension for n channels is:

$$J(x_n) = -\sum_{1...n} p(x_n) \log p(x_n)$$

Therefore, the total information content of the drug-response spectrograms is obtained in the limit:

$$J_\infty = \lim_{n \to \infty} J(x_n)$$

Figure 20:
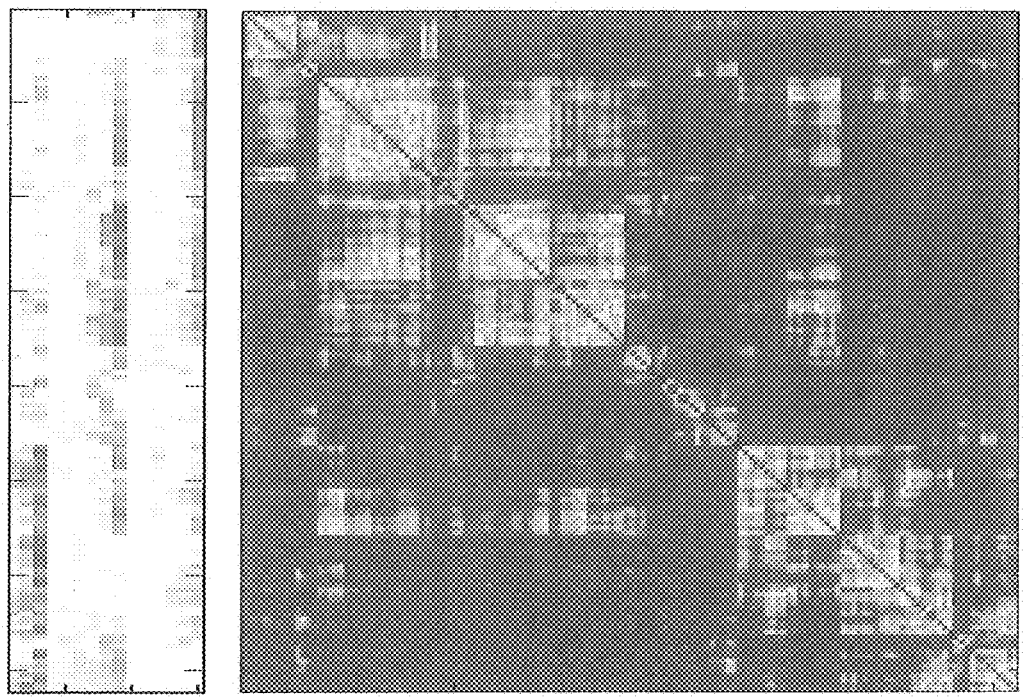
FIG. 20 shows a feature vector and hierarchical clustering similarity matrix for 144 different stimuli.
Figure 21:
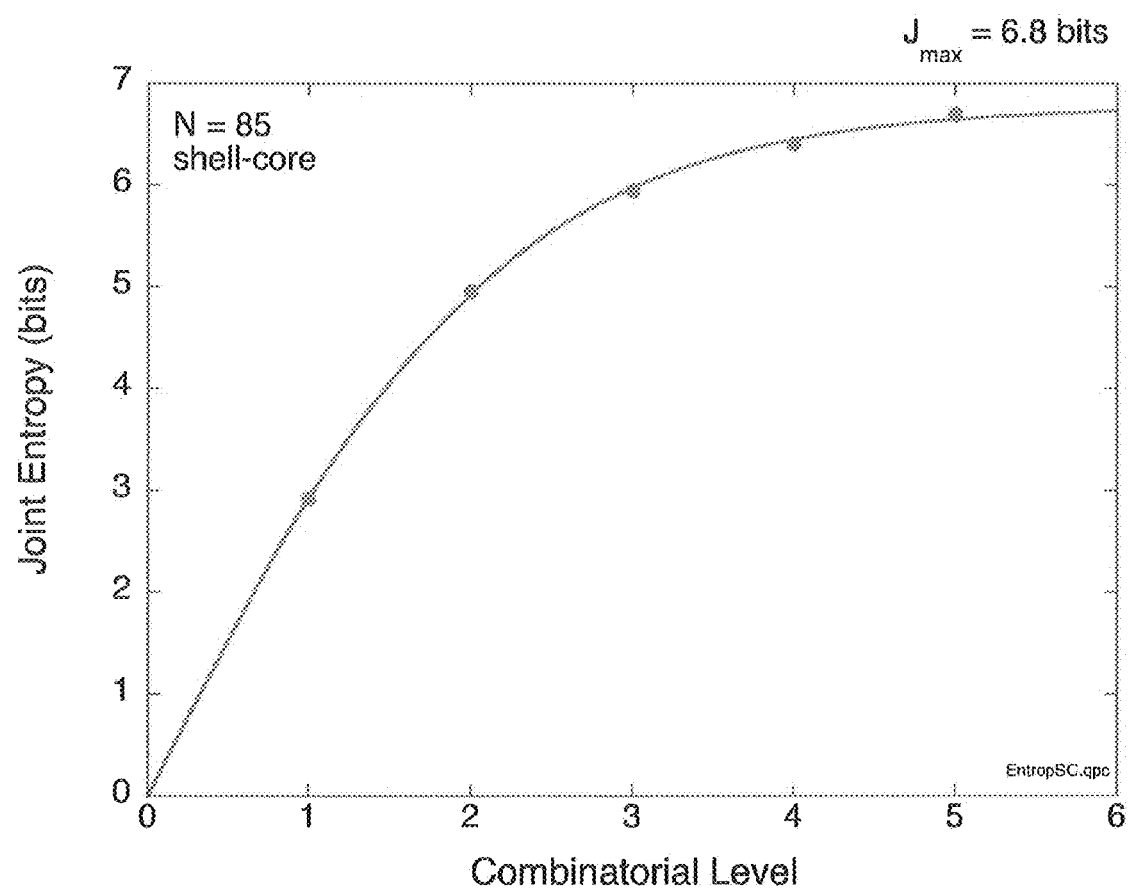
FIG. 21 is a graph of joint entropy for 170 drugs/doses/conditions including separate shell and core responses.

To calculate the total information content of tissue dynamics spectroscopy, an expanded data set of 170 different drugs, doses and conditions (and hence 170 spectrograms) is shown in FIG. 20. The joint entropy for n=2, 3, 4 and 5 is shown in FIG. 21. The asymptotic value in the limit of large n is 6.8 for the 170 spectrograms. Therefore, in the drug-response spectrograms, there are 6.8 bits of information per spectrogram. It is important to note that high-content screening (HCS) typically uses approximately this many channels. Therefore, tissue dynamics spectroscopy qualifies as a high-content screening approach for drug phenotypic profiling.

Application to Drug Screening

The drug-response spectrograms described above exhibit recognizable features that occur at characteristic frequency ranges at characteristic times after a dose and/or other stimuli is applied. Each spectrogram acts like a fingerprint, or more appropriately a voice print, showing a distinct pattern in response to the applied stimuli that is unique to the particular stimuli, which may be a particular drug and cell line. An analysis of the information content of the drug-response spectrograms based on Shannon entropy (as described in more detail above) indicates that more than 144 distinct spectrograms can be distinguished from one another, which can thereby be used to establish 144 different "classes" for compound/cell-line classifiers.

The present disclosure contemplates feature recognition and quantification of the drug-response spectrograms from projections of the spectrograms onto feature masks. The time axis of spectrograms primarily captures relaxation which is typically exponential. The frequency axis is the Fourier transform of the autocorrelation function, which is typically exponentially correlated. Thus, both the time and frequency axes are characterized by Laplace transforms for which there is no orthonormal basis. Consequently, in one aspect the systems and methods disclosed herein apply matched filtering in which characteristic regions of the spectrograms can be interpreted mechanistically. For instance, as discussed above low frequencies correspond to slow cellular shape changes like blebbing, mid frequencies correspond to membrane undulations and high frequencies correspond to membrane vesicles or internal organelle motions. These processes and frequencies present natural frequency ranges that are used to generate the feature masks, such as the masks shown in FIG. 7.

The inner product of each mask with a drug response spectrogram generates a feature vector that serves as the fingerprint for that particular drug. For instance, the feature vector for pH 9 is shown in FIG. 10. The feature vector illuminates the sensitivity of some features of the associated spectrogram, such as the organelle transport in the high frequency range after one hour, mid-frequency suppression of delayed undulations after four hours, delayed membrane at the low frequencies after 3½ hours and an initial hormetic response. The feature masks capture these changes in the feature vector for the particular stimuli response.

As described above, 15 feature vectors can be used corresponding to five frequency ranges across three time frames (although other frequency and time frame divisions can be utilized) and a similarity matrix is constructed from the correlation coefficients among the many pairs of feature vectors for different drugs and cell lines. A clustering algorithm (such as unsupervised hierarchical clustering) can be applied to the similarity matrix to order the tissue-response spectrograms of the different drugs and cell lines into groups based on the similarity of their response. The result is a clustered matrix that exhibits a block diagonal structure which is indicative that groups with high similarity have little overlap with other groups. By comparing a feature vector with the groupings it is possible to assign physiological attributes to the different groups. It is this quasi-orthogonality among the groups that provides the basis for phenotypic classification schemes in which a new lead compound of unknown mechanism may be compared against a reference compound library of dynamic tissue response spectrograms having known mechanisms of action.

To improve on the results from the clustering approach, the present system and method contemplates the use of multidimensional scaling to more faithfully represent the closeness and farness of compound/cell type groupings and to display the information in a readily understandable format. The result is a two dimensional map with nodes corresponding to stimuli distributed in a manner that retains the order of distances found in the similarity matrix, such as the Venn diagram shown in FIG. 14. Similar drug responses are grouped closely and farther from other unrelated drug responses. The map or Venn diagram thus provides a ready means to determine the expected phenotypic response of a new drug based on its proximity to other drugs in a grouping. For instance, if a new condition is OSM 154, a quick review of the map of FIG. 14 would reveal that the phenotypic response is blebbing and similar to the response of pH6, among other drugs/doses.

The feature masks, feature vectors, similarity matrices, clustering and multi-dimensional scaling all readily lend themselves to implementation in software. Thus, the drug screening process can be significantly automated from the generation of the spectrogram for a new drug/stimuli to the presentation of a Venn diagram similar to FIG. 14 from which the expected physiological response of a new drug can be readily discerned. The systems and methods disclosed herein can thus significantly reduce the amount of time required to assess a new drug. More importantly the multi-dimensional scaling approaches implemented herein more accurately align drugs/conditions having similar physiological responses, which can significantly reduce, if not eliminate, the risk of false positives and false negatives.

A library of known drugs/conditions and associated spectrograms can provide the foundation for the analysis of a new drug/stimuli/condition. All of the known drugs/conditions can be incorporated into a similarity matrix with the spectrogram of one or more new drugs/conditions to produce the clustered matrices and maps described above. In other words, as new drugs are categorized based on their physiological response they can be added to the library from which comparisons can be made for future drugs/conditions. Since the methods described herein can be readily implemented in software, the time required to validate or screen a new drug can be significantly reduced.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

REFERENCES

[1] C. Ainsworth, "NETWORKING FOR NEW DRUGS," *Nature Medicine*, vol. 17, pp. 1166-1168, October 2011.

[2] C. T. Keith, A. A. Borisy, and B. R. Stockwell, "Multi-component therapeutics for networked systems," *Nature Reviews Drug Discovery*, vol. 4, pp. 71-U10, January 2005.

[3] D. C. Swinney and J. Anthony, "How were new medicines discovered?," *Nature Reviews Drug Discovery*, vol. 10, pp. 507-519, July 2011.

[4] P. Hamer, S. Leenstra, C. J. F. Van Noorden, and A. H. Zwinderman, "Organotypic Glioma Spheroids for Screening of Experimental Therapies: How Many Spheroids and Sections are Required?," *Cytometry Part A*, vol. 75A, pp. 528-534, June 2009.

[5] J. Poland, P. Sinha, A. Siegert, M. Schnolzer, U. Korf, and S. Hauptmann, "Comparison of protein expression profiles between monolayer and spheroid cell culture of HT-29 cells revealed fragmentation of CK18 in three-dimensional cell culture," *Electrophoresis*, vol. 23, pp. 1174-1184, April 2002.

[6] K. Dardousis, C. Voolstra, M. Roengvoraphoj, A. Sekandarzad, S. Mesghenna, J. Winkler, Y. Ko, J. Hescheler, and A. Sachinidis, "Identification of differentially expressed genes involved in the formation of multicellular tumor spheroids by HT-29 colon carcinoma cells," *Molecular Therapy*, vol. 15, pp. 94-102, January 2007.

[7] N. A. L. Cody, M. Zietarska, A. Filali-Mouhim, D. M. Provencher, A. M. Mes-Masson, and P. N. Tonin, "Influence of monolayer, spheroid, and tumor growth conditions on chromosome 3 gene expression in tumorigenic epithelial ovarian cancer cell lines," *Bmc Medical Genomics*, vol. 1, Aug. 7, 2008.

[8] M. Zietarska, C. M. Maugard, A. Filali-Mouhim, M. Alam-Fahmy, P. N. Tonin, D. M. Provencher, and A. M. Mes-Masson, "Molecular description of a 3D in vitro model for the study of epithelial ovarian cancer (EOC)," *Molecular Carcinogenesis*, vol. 46, pp. 872-885, October 2007.

[9] T. T. Chang and M. Hughes-Fulford, "Monolayer and Spheroid Culture of Human Liver Hepatocellular Carcinoma Cell Line Cells Demonstrate Distinct Global Gene Expression Patterns and Functional Phenotypes," *Tissue Engineering Part A*, vol. 15, pp. 559-567, March 2009.

[10] M. Shimada, Y. Yamashita, S. Tanaka, K. Shirabe, K. Nakazawa, H. Ijima, R. Sakiyama, J. Fukuda, K. Funatsu, and K. Sugimachi, "Characteristic gene expression induced by polyurethane foam/spheroid culture of hepatoma cell line, Hep G2 as a promising cell source for bioartificial liver," *Hepato-Gastroenterology*, vol. 54, pp. 814-820, April-May 2007.

[11] Y. Yamashita, M. Shimada, N. Harimoto, S. Tanaka, K. Shirabe, H. Ijima, K. Nakazawa, J. Fukuda, K. Funatsu, and Y. Maehara, "cDNA microarray analysis in hepatocyte differentiation in Huh 7 cells," *Cell Transplantation*, vol. 13, pp. 793-799, 2004.

[12] L. Gaedtke, L. Thoenes, C. Culmsee, B. Mayer, and E. Wagner, "Proteomic analysis reveals differences in protein expression in spheroid versus monolayer cultures of low-passage colon carcinoma cells," *Journal of Proteome Research*, vol. 6, pp. 4111-4118, November 2007.

[13] A. Frankel, R. Buckman, and R. S. Kerbel, "Abrogation of taxol-induced G(2)-M arrest and apoptosis in human ovarian cancer cells grown as multicellular tumor spheroids," *Cancer Research*, vol. 57, pp. 2388-2393, Jun. 15, 1997.

[14] L. A. Hazlehurst, T. H. Landowski, and W. S. Dalton, "Role of the tumor microenvironment in mediating de novo resistance to drugs and physiological mediators of cell death," *Oncogene*, vol. 22, pp. 7396-7402, Oct. 20, 2003.

[15] I. Serebriiskii, R. Castello-Cros, A. Lamb, E. A. Golemis, and E. Cukierman, "Fibroblast-derived 3D matrix differentially regulates the growth and drug-responsiveness of human cancer cells," *Matrix Biology*, vol. 27, pp. 573-585, July 2008.

[16] L. David, V. Dulong, D. Le Cerf, L. Cazin, M. Lamacz, and J. P. Vannier, "Hyaluronan hydrogel: An appropriate three-dimensional model for evaluation of anticancer drug sensitivity," *Acta Biomaterialia*, vol. 4, pp. 256-263, March 2008.

[17] R. C. Youngquist, S. Carr, and D. E. N. Davies, "Optical coherence-domain reflectometry: a new optical evaluation technique," *Opt. Lett.*, vol. 12, p. 158, 1987.

[18] M. Suissa, C. Place, E. Goillot, and E. Freyssingeas, "Internal dynamics of a living cell nucleus investigated by dynamic light scattering," *European Physical Journal E*, vol. 26, pp. 435-448, August 2008.

[19] X. L. Nan, P. A. Sims, and X. S. Xie, "Organelle tracking in a living cell with microsecond time resolution and nanometer spatial precision," *Chemphyschem*, vol. 9, pp. 707-712, Apr. 4, 2008.

[20] K. J. Karnaky, L. T. Garretson, and R. G. Oneil, "Video-Enhanced Microscopy of Organelle Movement in an Intact Epithelium," *Journal of Morphology*, vol. 213, pp. 21-31, July 1992.

[21] N. A. Brazhe, A. R. Brazhe, A. N. Pavlov, L. A. Erokhova, A. I. Yusipovich, G. V. Maksimov, E. Mosekilde, and O. V. Sosnovtseva, "Unraveling cell processes: Interference imaging interwoven with data analysis," *Journal of Biological Physics*, vol. 32, pp. 191-208, October 2006.

[22] B. Trinczek, A. Ebneth, and E. Mandelkow, "Tau regulates the attachment/detachment but not the speed of motors in microtubule-dependent transport of single

[23] F. Brochard and J. F. Lennon, "Frequency Spectrum of Flicker Phenomenon in Erythrocytes," *Journal De Physique*, vol. 36, pp. 1035-1047, 1975.

[24] H. Strey and M. Peterson, "Measurement of Erythrocyte-Membrane Elasticity by Flicker Eigenmode Decomposition," *Biophysical Journal*, vol. 69, pp. 478-488, August 1995.

[25] A. Zilker, M. Ziegler, and E. Sackmann, "Spectral-Analysis of Erythrocyte Flickering in the 0.3-4-Mu-M-1 Regime by Microinterferometry Combined with Fast Image-Processing," *Physical Review A*, vol. 46, pp. 7998-8002, Dec. 15, 1992.

[26] M. A. Peterson, H. Strey, and E. Sackmann, "Theoretical and Phase-Contrast Microscopic Eigenmode Analysis of Erythrocyte Flicker—Amplitudes," *Journal De Physique Ii*, vol. 2, pp. 1273-1285, May 1992.

[27] Y. Z. Yoon, H. Hong, A. Brown, D. C. Kim, D. J. Kang, V. L. Lew, and P. Cicuta, "Flickering Analysis of Erythrocyte Mechanical Properties: Dependence on Oxygenation Level, Cell Shape, and Hydration Level," *Biophysical Journal*, vol. 97, pp. 1606-1615, Sep. 16, 2009.

[28] J. Evans, W. Gratzer, N. Mohandas, K. Parker, and J. Sleep, "Fluctuations of the red blood cell membrane: Relation to mechanical properties and lack of ATP dependence," *Biophysical Journal*, vol. 94, pp. 4134-4144, May 15, 2008.

[29] V. Racine, M. Sachse, J. Salamero, V. Fraisier, A. Trubuil, and J. B. Sibarita, "Visualization and quantification of vesicle trafficking on a three-dimensional cytoskeleton network in living cells," *Journal Of Microscopy-Oxford*, vol. 225, pp. 214-228, March 2007.

[30] Ifeachor, E. and B. Jervis (2001). *Digital Signal Processing: A Practical Approach*, Prentice Hall.

[31] Nolte, D. D., R. An, et al. (2011). "Holographic tissue dynamics spectroscopy." *Journal of Biomedical Optics* 16(8): 087004-087013.

[32] Johnson, R. A. (2001). *Applied Multivariate Statistical Analysis*, Prentice Hall.

[33] Andreopoulos, B., A. J. An, et al. (2009). "A roadmap of clustering algorithms: finding a match for a biomedical application." *Briefings in Bioinformatics* 10(3): 297-314.

[34] Lampert, T. A. and S. E. M. O'Keefe (2010). "A survey of spectrogram track detection algorithms." *Applied Acoustics* 71(2): 87-100.

[35] Venkatasubramanian, R., M. A. Henson, et al. (2006). "Incorporating energy metabolism into a growth model of multicellular tumor spheroids." *Journal of Theoretical Biology* 242(2): 440-453.

[36] Mellor, H. R., D. J. P. Ferguson, et al. (2005). "A model of quiescent tumour microregions for evaluating multicellular resistance to chemotherapeutic drugs." *British Journal of Cancer* 93(3): 302-309.

[37] Fayad, W., L. Rickardson, et al. (2011). "Identification of Agents that Induce Apoptosis of Multicellular Tumour Spheroids: Enrichment for Mitotic Inhibitors with Hydrophobic Properties." *Chemical Biology & Drug Design* 78(4): 547-557.

[38] Zhou, J., T. Schmid, et al. (2006). "Tumor hypoxia and cancer progression." *Cancer Letters* 237(1): 10-21.

[39] Gillies, R. J. and R. A. Gatenby (2007). "Hypoxia and adaptive landscapes in the evolution of carcinogenesis." *Cancer and Metastasis Reviews* 26(2): 311-317.

[40] Sullivan, R. and C. H. Graham (2007). "Hypoxia-driven selection of the metastatic phenotype." *Cancer and Metastasis Reviews* 26(2): 319-331.

[41] Gort, E. H., A. J. Groot, et al. (2008). "Hypoxic regulation of metastasis via hypoxia-inducible factors." *Current Molecular Medicine* 8(1): 60-67.

[42] Klymkowsky, M. W. and P. Savagner (2009). "Epithelial-Mesenchymal Transition A Cancer Researcher's Conceptual Friend and Foe." *American Journal of Pathology* 174(5): 1588-1593.

[43] Yan, W., Y. Fu, et al. (2009). "PI3 kinase/Akt signaling mediates epithelial-mesenchymal transition in hypoxic hepatocellular carcinoma cells." *Biochemical and Biophysical Research Communications* 382(3): 631-636.

[44] Farhat, G., A. Mariampillai, et al. (2011). "Detecting apoptosis using dynamic light scattering with optical coherence tomography." *Journal of Biomedical Optics* 16(7).

What is claimed is:

1. A method of evaluating a drug, comprising:
applying a drug to a living body in which a functional response of the living body to the drug is under evaluation;
generating a differential spectrogram which plots a differential relative spectral density for a given frequency at a time t relative to an initial time $t_0$ using motility contrast imaging of the living body as it responds to the application of the drug;
applying a plurality of feature masks to the spectrogram for the drug under evaluation wherein each feature mask identifies a portion of the spectrogram;
applying the plurality of feature masks to a plurality of differential spectrograms wherein each of the plurality of differential spectrograms is obtained by applying a stimulus to a living body wherein the living body has a known response to the stimulus;
generating a feature vector for the drug under evaluation by assigning a numerical value for each of the plurality of feature masks wherein the assigned numerical value is related to the strength and sign of the response of the living body for that portion of the spectrogram identified by the feature mask;
generating a feature vector for each of the plurality of differential spectrograms generated by applying stimuli to the living body wherein each feature vector is created by assigning a numerical value for each of the plurality of feature masks wherein the assigned numerical value is related to the strength and sign of the response of the living body for that portion of the spectrogram identified by the feature mask; and
evaluating the drug under evaluation by comparing the feature vector for the drug under evaluation with the feature vectors for the plurality of stimuli to determine whether the living body exhibits a known functional response to the drug under evaluation, and if so, selecting and using the drug under evaluation for treatment of a patient or further testing.

2. The method of claim 1, wherein application of at least one of the plurality of the plurality of feature masks includes obtaining a frequency value through an ensemble average over many spectrograms.

3. The method of claim 2, wherein the frequencies are obtained through a level-set approach that is averaged over many spectrograms.

4. The method of claim 3, wherein the level-set is set to zero.

5. The method of claim 1, wherein the feature masks are selected morphometrically using the spectrogram to which the feature mask will be applied to define its own masked regions by identifying regions of common response to thereby define the feature masks.

6. The method of claim 1, wherein quantitative index values are constructed for individual spectrograms as a function of the assigned numerical values from a plurality of the feature masks.

7. The method of claim 6, wherein the quantitative index value is an apoptotic index representative of apoptotic activity in the living sample.

8. The method of claim 7, wherein the apoptotic index value is a function of an assigned numerical value of a feature mask identifying a low-frequency portion of the spectrogram and an assigned numerical value of a feature mask identifying a high-frequency portion of the spectrogram.

9. The method of claim 1, wherein Shannon entropy is used to optimize the selection of one or more feature masks used to generate the feature vector.

10. The method of claim 9, wherein the entropy of many sets of feature masks are calculated and compared, and the feature set leading to the largest information content is selected to generate the plurality of feature vectors.

11. A method for creating a phenotypic profile useful for drug screening, comprising:
  applying a drug to a living body in which a functional response of the living body to the drug is under evaluation;
  generating a differential spectrogram which plots a differential relative spectral density for a given frequency at a time t relative to an initial time $t_o$ using motility contrast imaging of the living body as it responds to the application of the drug;
  applying a plurality of feature masks to the spectrogram for the drug under evaluation wherein each feature mask identifies a portion of the spectrogram;
  generating a feature vector for the drug under evaluation by assigning a numerical value for each of the plurality of feature masks wherein the assigned numerical value is related to the strength and sign of the response of the living body for that portion of the spectrogram identified by the feature mask;
  using the feature vector to generate a phenotypic profile for the drug under evaluation;
  using the phenotypic profile to make a determination whether the drug under evaluation is suitable for use in treatment of a patient or further testing; and
  if the drug under evaluation is suitable, using the drug for treatment of a patient or further testing.

12. The method of claim 11, wherein the phenotypic profile is generated through multidimensional scaling (MDS).

13. The method claim 12, wherein a Venn diagram is overlaid on the MDS graph.

14. The method of claim 13, where the Venn diagram has physiological interpretations based on the physiological responses isolated in the feature vector quantities.

15. The method of claim 12, wherein the MDS space is defined in terms of trajectories of a continuously variable condition.

16. The method of claim 15, wherein the continuously variable condition is pH.

17. The method of claim 15, wherein the continuously variable condition is osmolarity.

18. A method for creating a phenotypic profile useful for drug screening, comprising:
  applying a drug to a living body in which a functional response of the living body to the drug is under evaluation;
  generating a differential spectrogram which plots a differential relative spectral density for a given frequency at a time t relative to an initial time $t_o$ using motility contrast imaging of the living body as it responds to the application of the drug;
  applying a plurality of feature masks to the spectrogram for the drug under evaluation wherein each feature mask identifies a portion of the spectrogram;
  applying the plurality of feature masks to a plurality of differential spectrograms wherein each of the plurality of differential spectrograms is obtained by applying a stimulus to a living body wherein the living body has a known response to the stimulus;
  generating a feature vector for the drug under evaluation by assigning a numerical value for each of the plurality of feature masks wherein the assigned numerical value is related to the strength and sign of the response of the living body for that portion of the spectrogram identified by the feature mask;
  generating a feature vector for each of the plurality of differential spectrograms generated by applying stimuli to the living body wherein each feature vector is created by assigning a numerical value for each of the plurality of feature masks wherein the assigned numerical value is related to the strength and sign of the response of the living body for that portion of the spectrogram identified by the feature mask;
  generating a similarity matrix from the feature vector of the drug under evaluation and from the plurality of feature vectors of the plurality of stimuli wherein each row of the similarity matrix is one of the feature vectors;
  re-ordering the similarity matrix to group common drug responses together;
  generating a phenotypic profile for the drug under evaluation based upon the grouping of the feature vectors;
  using the phenotypic profile to make a determination whether the drug under evaluation is suitable for use in treatment of a patient or further testing; and
  if the drug under evaluation is suitable, using the drug for treatment of a patient or further testing.

19. The method of claim 18, wherein the step of re-ordering the similarity matrix includes applying hierarchical clustering to the similarity matrix to produce a nearly block-diagonal matrix with groups of spectrograms that share common physiological responses.

20. The method of claim 18, wherein the step of re-ordering the similarity matrix includes applying multi-dimensional scaling (MDS) to the similarity matrix that maintains the spatial near-far relationships among drugs in each grouping and wherein the inner product of each row is used when defining the spatial near-far relationships.

21. The method of claim 20, wherein the multi-dimensional scaling includes simulated annealing of a MDS cost function.

22. The method of claim 20, wherein the result of the MDS is a map of nodes corresponding to each drug and condition in which nodes corresponding to similar physiological responses are grouped closely and far from unrelated drug responses.

23. The method of claim 22, further comprising generating a Venn diagram from the map based on common physiological features.

24. The method of claim 18, wherein generating a similarity matrix includes:
generating feature masks corresponding to predetermined physiological responses of the living body;
applying the feature masks to the spectrograms to generate a feature vector for each spectrogram; and
combining the feature vectors to produce the similarity matrix.

25. The method of claim 24, wherein the feature masks correspond to recognizable physiological responses that occur in characteristic frequency ranges at characteristic times.

26. The method of claim 25, wherein the characteristic frequency ranges include at least three ranges centered on 0.01 Hz (low), 0.1 Hz (mid) and 1 Hz (high).

27. The method of claim 25, wherein the characteristic times include short times (0 to 50 minutes) for fast response, mid times (50 to 150 minutes) for slower response and long times (150 to 350 minutes) for long-term response.

* * * * *